US006670134B1

(12) United States Patent
Gil et al.

(10) Patent No.: US 6,670,134 B1
(45) Date of Patent: Dec. 30, 2003

(54) HUMAN EP$_3$ PROSTAGLANDIN RECEPTOR

(75) Inventors: Daniel W. Gil, Corona Del Mar, CA (US); John W. Regan, Tucson, AZ (US)

(73) Assignees: Allergan, Inc., Irvine, CA (US); Arizona Board of Regents, Tucson, AZ (US)

( * ) Notice: Subject to any disclaimer, the term of this patent is extended or adjusted under 35 U.S.C. 154(b) by 187 days.

(21) Appl. No.: 09/661,758

(22) Filed: Sep. 14, 2000

Related U.S. Application Data

(62) Division of application No. 09/363,783, filed on Jul. 29, 1999, now Pat. No. 6,197,933, which is a division of application No. 08/155,055, filed on Nov. 19, 1993, now Pat. No. 6,057,433.

(51) Int. Cl.[7] .................. G01N 33/53; G01N 33/567; C07K 1/00; C07K 14/00; C07K 17/00
(52) U.S. Cl. .................. 435/7.1; 435/7.2; 530/350
(58) Field of Search .................. 435/7.1, 7.2; 530/350

(56) References Cited

FOREIGN PATENT DOCUMENTS

| EP | 0557966 A1 | 2/1993 |
|----|------------|--------|
| WO | WO95 00551 | 1/1995 |
| WO | WO95 00552 | 1/1995 |
| WO | WO95/00552 | 1/1995 |

OTHER PUBLICATIONS

Chen, et al. "Prostanoid Inhibition of Canine Parietal Cells: Mediation by the Inhibitory Guanosine Triphosphate–Binding Protein of Adenylate Cyclase" *Gastroenterology* 94: pp. 1121–1129 (1988).

Giles, et al. "More selective ligans at eiconsanoid receptor subtypes improve prospects in inflammatory and cardiovascular research" *TIPS* 11: pp. 301–304 (1990).

Hébert, et al. "PGE$_2$ inhibits AVP–induced water flow in cortical collecting ducts by protein kinase C activation"*Am. Physiol. Soc.* pp. F318–F325 (1990).

Hedqvist, et al. "Prostaglandin–induced neurotransmission failure in the field–stimulated, isolated vas deferens" *Neuropharm.* 11: pp. 177–187 (1972).

Hirata, et al. "Cloning and expression of cDNA for a human thromboxane A$_2$ receptor" *Nature* 349: pp. 617–620 (1991).

Honda, et al. "Cloning and Expression of a cDNA for Mouse Prostaglandin E Receptor EP$_2$ Subtype*" *J. Biol. Chem.* 2618:11 pp. 7759–7762 (1993).

Link, et al. "Cloning of Two Mouse Genes encoding $\alpha_2$–C10 Homolog Responsible for an Interspecies Variation in Antagonist Binding" *Mol. Pharmacol.* 42: pp. 16–27 (1992).

Matthews et al. "Prostaglandin–induced neurotransmission failure in the field stimulated, isolated vas deferens" *Neuropharmacology* 11: pp. 177–187 (1972).

Namba, et al. "Alternative splicing of C–terminal tail of prostaglandin E receptor subtype EP3 determines G–protein Specificity" *Nature* 365: pp. 166–170 (1993).

Oksenberg, et al. "A single amino–acid difference confers major pharmacological variation between human and rodent 5–HT$_{1B}$ receptors" *Nature* 360: pp. 161–163 (1992).

Samuelsson, et al. "A simple phase–extraction assay for chloramphenicol acyltransferase activity" *Gene* 67: pp. 271–277 (1988).

Seed, et al. "A simple phase–extraction assay for chloramphenicol acyltransferase activity" *Gene* 67: pp. 271–277 (1988).

Smith, et al. Review Article: "The eiconsanoids and their biochemical mechanisms of action" *Biochem. J.* 259: pp. 315–324 (1989).

Smith, et al. "Prostanoid biosynthesis and mechanisms of action" *Amer. Physio. Soc* pp. F181–F191 (1992).

Sonnenburg, et al. "Regulation of Cyclic AMP Metabolism in Rabbit Cortical Collecting Tubule Cells by Prostaglandins*" *J. Biol. Chem.* 263:13 pp. 6155–6160 (1988).

Sugimoto, et al. "Cloning and Expression of a cDNA for Mouse Prostaglandin E Receptor EP$_3$ Subtype *" *J. Biol. Chem.* 267:10 pp. 6463–6466 (1992).

Sugimoto, et al. "Two Isoforms of the EP$_3$ Receptor with Different Carboxyl–terminal Domains" *J. Biol. Chem.* 268: pp. 2712–2718 (1993).

Tynan, et al. "On the Multiplicity of Platelet Prostaglandin Receptors II PGE$_2$., and Hydantoin Analogs" *Prostaglandis* 27:5 pp. 683–697 (1984).

Woodward, et al. "Intraocular pressure effects of selective prostanoid receptor agonists involve different receptor subtypes according to radioligand binding studies" *J. Lipid Mediators* 6: pp. 545–553 (1993).

Negishi, et al. "Functional interaction of prostaglandin E receptor EP$_3$ subtype with guanine nucleotide–binding proteins, showing low–affinity ligand binding" *Biochimica et Biophysica Acta* 1175: pp. 343–350 (1993).

Negishi, et al. "Two isoforms of Prostaglandin E Receptor EP$_3$ Subtype" *J. Bio. Chem.* 268:13: pp. 9517–9521 (1993).

Takeuchi, et al. "Molecular Cloning and Intrarenal Localization of Rat Prostaglandin E$_2$ Receptor EP$_3$ Subtype[1]"*Biochem. and Biophys. Res. Comm.* 194:2 pp. 885–891 (1993).

(List continued on next page.)

Primary Examiner—Gary Kunz
Assistant Examiner—Robert S. Landsman
(74) Attorney, Agent, or Firm—Carlos A. Fisher; Martin A. Voet; Robert J. Baran

(57) ABSTRACT

A gene encoding the human EP$_3$ prostaglandin receptor has been cloned and sequenced. The protein encoded by this gene has seven transmembrane domains and is 81% homologous to the murine EP$_3$ receptor. Two variants that differ in their carboxy terminal coding sequence, and one variant that differs in its 3' untranslated sequence only, have also been cloned. The proteins, when expressed in eukaryotic cells, are capable of binding prostaglandins and their agonists and regulating adenylate cyclase activity in response to prostaglandins.

7 Claims, 3 Drawing Sheets

OTHER PUBLICATIONS

Kedzie, K.M., et al.; FASEB Journal; vol. 8, No. 7, Apr. 1994, P. A1386; "Human EP-3 receptor variants differ at their carboxyl termini"; & 85th Annual Meeting of the American Society for Biochemistry and Molecular Biology, May 21–25, 1994, See Abstract 737.

Oksenberg et al, "A single amino–acid difference confers major pharmacological variation between human and rodent 5–HT $_{1B}$receptors", Nature, 360:161–163 (1992).

Namba et al, Biochem and Biophy. Res. Commun., vol. 184, pp. 1197–1203, 1993.

Namba et al, The Journal of Biol. Chem., vol. 269, pp. 9986–9992, 1994.

Adam, M., et al. Cloning and expression of three isoforms of the human EP3 prostanoid receptor, FEBS Letters, 338. No. 2 pp. 170–174, 1994 (Jan. 31, 1994).

Rudinger J., et al. Characteristics of the amino acids as components of a peptide hormone sequence in Peptide Hormones, pp. 1–7, Edited by Parsons, JA: Mill Hill, London, 1976.

Senior et al. Br. J. Pharmacol. 102:747–753, 1991.*

Matthews et al. Br. J. Pharmacol. 108:363–369, 1993.*

* cited by examiner

```
                         SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: Sense primer (ix) FEATURE:
         (A) NAME/KEY: modified_base (inosine)
         (B) LOCATION: 12

(ix) FEATURE:
         (A) NAME/KEY: modified_base (inosine)
         (B) LOCATION: 15

(ix) FEATURE:
         (A) NAME/KEY: modified_base (inosine)
         (B) LOCATION: 18

(ix) FEATURE:
         (A) NAME/KEY: modified_base (inosine)
         (B) LOCATION: 24

(xi) SEQUENCE DESCRIPTION: SEQ ID NO: 1:

GAYCCGTCGK GNCGNCTNTG YMSNTT                                              26

(2) INFORMATION FOR SEQ ID NO: 2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vii) IMMEDIATE SOURCE:
         (B) CLONE: Antisense primer
```

(ix) FEATURE:
    (A) NAME/KEY: modified_base (inosine)
    (B) LOCATION: 9

(xi) SEQUENCE DESCRIPTION: SEQ ID NO: 2:

ACRCACATNA TNCCCATNAR YTG                                        23

(2) INFORMATION FOR SEQ ID NO: 3:

(i) SEQUENCE CHARACTERISTICS:
        (A) LENGTH: 1651 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 57..1226

(xi) SEQUENCE DESCRIPTION: SEQ ID NO: 3:

```
TGCCCCCTCC CGCTGCGGCT CTCTGGACGC CATCCCCTCC TCACCTCGAA GCCAAC            56

ATG AAG GAG ACC CGG GGC TAC GGA GGG GAT GCC CCC TTC TGC ACC CGC         104
Met Lys Glu Thr Arg Gly Tyr Gly Gly Asp Ala Pro Phe Cys Thr Arg
  1               5                  10                  15

CTC AAC CAC TCC TAC ACA GGC ATG TGG GCG CCC GAG CGT TCC GCC GAG         152
Leu Asn His Ser Tyr Thr Gly Met Trp Ala Pro Glu Arg Ser Ala Glu
             20                  25                  30

GCG CGG GGC AAC CTC ACG CGC CCT CCA GGG TCT GGC GAG GAT TGC GGA         200
Ala Arg Gly Asn Leu Thr Arg Pro Pro Gly Ser Gly Glu Asp Cys Gly
         35                  40                  45

TCG GTG TCC GTG GCC TTC CCG ATC ACC ATG CTG CTG ACT GGT TTC GTG         248
Ser Val Ser Val Ala Phe Pro Ile Thr Met Leu Leu Thr Gly Phe Val
     50                  55                  60

GGC AAC GCA CTG GCC ATG CTG CTC GTG TCG CGC AGC TAC CGG CGC CGG         296
Gly Asn Ala Leu Ala Met Leu Leu Val Ser Arg Ser Tyr Arg Arg Arg
 65                  70                  75                  80

GAG AGC AAG CGC AAG AAG TCC TTC CTG CTG TGC ATC GGC TGG CTG GCG         344
Glu Ser Lys Arg Lys Lys Ser Phe Leu Leu Cys Ile Gly Trp Leu Ala
                 85                  90                  95

CTC ACC GAC CTG GTC GGG CAG CTT CTC ACC ACC CCG GTC GTC ATC GTC         392
Leu Thr Asp Leu Val Gly Gln Leu Leu Thr Thr Pro Val Val Ile Val
            100                 105                 110

GTG TAC CTG TCC AAG CAG CGT TGG GAG CAC ATC GAC CCG TCG GGG CGG         440
Val Tyr Leu Ser Lys Gln Arg Trp Glu His Ile Asp Pro Ser Gly Arg
        115                 120                 125

CTC TGC ACC TTT TTC GGG CTG ACC ATG ACT GTT TTC GGG CTC TCC TCG         488
Leu Cys Thr Phe Phe Gly Leu Thr Met Thr Val Phe Gly Leu Ser Ser
    130                 135                 140

TTG TTC ATC GCC AGC GCC ATG GCC GTC GAG CGG GCG CTG GCC ATC AGG         536
Leu Phe Ile Ala Ser Ala Met Ala Val Glu Arg Ala Leu Ala Ile Arg
145                 150                 155                 160

GCG CCG CAC TGG TAT GCG AGC CAC ATG AAG ACG CGT GCC ACC CGC GCT         584
Ala Pro His Trp Tyr Ala Ser His Met Lys Thr Arg Ala Thr Arg Ala
                165                 170                 175

GTG CTG CTC GGC GTG TGG CTG GCC GTG CTC GCC TTC GCC CTG CTG CCG         632
Val Leu Leu Gly Val Trp Leu Ala Val Leu Ala Phe Ala Leu Leu Pro
            180                 185                 190
```

```
GTG CTG GGC GTG GGC CAG TAC ACC GTC CAG TGG CCC GGG ACG TGG TGC      680
Val Leu Gly Val Gly Gln Tyr Thr Val Gln Trp Pro Gly Thr Trp Cys
            195                 200                 205

TTC ATC AGC ACC GGG CGA GGG GGC AAC GGG ACT AGC TCT TCG CAT AAC      728
Phe Ile Ser Thr Gly Arg Gly Gly Asn Gly Thr Ser Ser Ser His Asn
    210                 215                 220

TGG GGC AAC CTT TTC TTC GCC TCT GCC TTT GCC TTC CTG GGG CTC TTG      776
Trp Gly Asn Leu Phe Phe Ala Ser Ala Phe Ala Phe Leu Gly Leu Leu
225                 230                 235                 240

GCG CTG ACA GTC ACC TTT TCC TGC AAC CTG GCC ACC ATT AAG GCC CTG      824
Ala Leu Thr Val Thr Phe Ser Cys Asn Leu Ala Thr Ile Lys Ala Leu
                245                 250                 255

GTG TCC CGC TGC CGG GCC AAG GCC ACG GCA TCT CAG TCC AGT GCC CAG      872
Val Ser Arg Cys Arg Ala Lys Ala Thr Ala Ser Gln Ser Ser Ala Gln
            260                 265                 270

TGG GGC CGC ATC ACG ACC GAG ACG GCC ATT CAG CTT ATG GGG ATC ATG      920
Trp Gly Arg Ile Thr Thr Glu Thr Ala Ile Gln Leu Met Gly Ile Met
        275                 280                 285

TGC GTG CTG TCG GTC TGC TGG TCT CCG CTC CTG ATA ATG ATG TTG AAA      968
Cys Val Leu Ser Val Cys Trp Ser Pro Leu Leu Ile Met Met Leu Lys
    290                 295                 300

ATG ATC TTC AAT CAG ACA TCA GTT GAG CAC TGC AAG ACA CAC ACG GAG     1016
Met Ile Phe Asn Gln Thr Ser Val Glu His Cys Lys Thr His Thr Glu
305                 310                 315                 320

AAG CAG AAA GAA TGC AAC TTC TTC TTA ATA GCT GTT CGC CTG GCT TCA     1064
Lys Gln Lys Glu Cys Asn Phe Phe Leu Ile Ala Val Arg Leu Ala Ser
                325                 330                 335

CTG AAC CAG ATC TTG GAT CCT TGG GTT TAC CTG CTG TTA AGA AAG ATC     1112
Leu Asn Gln Ile Leu Asp Pro Trp Val Tyr Leu Leu Leu Arg Lys Ile
            340                 345                 350

CTT CTT CGA AAG TTT TGC CAG ATC AGG TAC CAC ACA AAC AAC TAT GCA     1160
Leu Leu Arg Lys Phe Cys Gln Ile Arg Tyr His Thr Asn Asn Tyr Ala
        355                 360                 365

TCC AGC TCC ACC TCC TTA CCC TGC CAG TGT TCC TCA ACC TTG ATG TGG     1208
Ser Ser Ser Thr Ser Leu Pro Cys Gln Cys Ser Ser Thr Leu Met Trp
    370                 375                 380

AGC GAC CAT TTG GAA AGA TGAGAAAAAG AAGACTCAGA GAGCAATTCT            1256
Ser Asp His Leu Glu Arg
385                 390

GGAGGCCGGC AAGTTCAGGA TCAGGGTGCC AGCAGATTCG GTGTCTGACT GGAGTGCAGT   1316

GGAGTGATTT CCGCTCACTG CAACCTTCAC CTCCTCCACT CACTGCAATC TTCGCCTCCT   1376

GGGTTCAAGT GATTCTCCTG CCTCAGCCTC CCAAGTAGCT GGAATTGCAC GATGCGCCAC   1436

AAGCCTGGCT AATTTTTGCA TTTTTAGTAG AGATGAGTTT CACCATGTTT GCCAGGCTGG   1496

TCTTGAACAC CTGACCTCAA GTAACCCACC CACCTTGGCC TCCCAAGAGC TGGGATTACA   1556

GGCATGAGCC AACGTGCCTG GCCATGTTCT GATCGTTTAA TGATAGCAAC ATTTAGTATT   1616

ATAGAGCATG AAAATGTCAA AGCGGCCCGG AATTC                              1651

(2) INFORMATION FOR SEQ ID NO: 4:

(i) SEQUENCE CHARACTERISTICS:
            (A) LENGTH: 390 amino acids
            (B) TYPE: amino acid
            (D) TOPOLOGY: linear (ii) MOLECULE TYPE: protein (xi) SEQUENCE DESCRIPTION: SEQ ID NO: 4:
```

-continued

```
Met Lys Glu Thr Arg Gly Tyr Gly Gly Asp Ala Pro Phe Cys Thr Arg
  1               5                  10                 15

Leu Asn His Ser Tyr Thr Gly Met Trp Ala Pro Glu Arg Ser Ala Glu
             20                  25                 30

Ala Arg Gly Asn Leu Thr Arg Pro Pro Gly Ser Gly Glu Asp Cys Gly
         35                  40                 45

Ser Val Ser Val Ala Phe Pro Ile Thr Met Leu Leu Thr Gly Phe Val
     50                  55                 60

Gly Asn Ala Leu Ala Met Leu Leu Val Ser Arg Ser Tyr Arg Arg Arg
 65                 70                  75                     80

Glu Ser Lys Arg Lys Lys Ser Phe Leu Leu Cys Ile Gly Trp Leu Ala
             85                  90                 95

Leu Thr Asp Leu Val Gly Gln Leu Leu Thr Thr Pro Val Val Ile Val
            100                 105                110

Val Tyr Leu Ser Lys Gln Arg Trp Glu His Ile Asp Pro Ser Gly Arg
            115                 120                125

Leu Cys Thr Phe Phe Gly Leu Thr Met Thr Val Phe Gly Leu Ser Ser
        130                 135                140

Leu Phe Ile Ala Ser Ala Met Ala Val Glu Arg Ala Leu Ala Ile Arg
145                 150                 155                    160

Ala Pro His Trp Tyr Ala Ser His Met Lys Thr Arg Ala Thr Arg Ala
                165                 170                175

Val Leu Leu Gly Val Trp Leu Ala Val Leu Ala Phe Ala Leu Leu Pro
            180                 185                190

Val Leu Gly Val Gly Gln Tyr Thr Val Gln Trp Pro Gly Thr Trp Cys
            195                 200                205

Phe Ile Ser Thr Gly Arg Gly Gly Asn Gly Thr Ser Ser Ser His Asn
    210                 215                 220

Trp Gly Asn Leu Phe Phe Ala Ser Ala Phe Ala Phe Leu Gly Leu Leu
225                 230                 235                240

Ala Leu Thr Val Thr Phe Ser Cys Asn Leu Ala Thr Ile Lys Ala Leu
                245                 250                255

Val Ser Arg Cys Arg Ala Lys Ala Thr Ala Ser Gln Ser Ser Ala Gln
            260                 265                270

Trp Gly Arg Ile Thr Thr Glu Thr Ala Ile Gln Leu Met Gly Ile Met
            275                 280                285

Cys Val Leu Ser Val Cys Trp Ser Pro Leu Leu Ile Met Met Leu Lys
            290                 295                300

Met Ile Phe Asn Gln Thr Ser Val Glu His Cys Lys Thr His Thr Glu
305                 310                 315                320

Lys Gln Lys Glu Cys Asn Phe Phe Leu Ile Ala Val Arg Leu Ala Ser
                325                 330                335

Leu Asn Gln Ile Leu Asp Pro Trp Val Tyr Leu Leu Leu Arg Lys Ile
            340                 345                350

Leu Leu Arg Lys Phe Cys Gln Ile Arg Tyr His Thr Asn Asn Tyr Ala
            355                 360                365

Ser Ser Ser Thr Ser Leu Pro Cys Gln Cys Ser Ser Thr Leu Met Trp
        370                 375                380

Ser Asp His Leu Glu Arg
385                 390
```

(2) INFORMATION FOR SEQ ID NO: 5:

(i) SEQUENCE CHARACTERISTICS:

(A) LENGTH: 1223 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (ix) FEATURE:
(A) NAME/KEY: CDS
(B) LOCATION: 57..1220

(xi) SEQUENCE DESCRIPTION: SEQ ID NO: 5:

```
TGCCCCCTCC CGCTGCGGCT CTCTGGACGC CATCCCCTCC TCACCTCGAA GCCAAC            56

ATG AAG GAG ACC CGG GGC TAC GGA GGG GAT GCC CCC TTC TGC ACC CGC         104
Met Lys Glu Thr Arg Gly Tyr Gly Gly Asp Ala Pro Phe Cys Thr Arg
  1               5                  10                  15

CTC AAC CAC TCC TAC ACA GGC ATG TGG GCG CCC GAG CGT TCC GCC GAG         152
Leu Asn His Ser Tyr Thr Gly Met Trp Ala Pro Glu Arg Ser Ala Glu
             20                  25                  30

GCG CGG GGC AAC CTC ACG CGC CCT CCA GGG TCT GGC GAG GAT TGC GGA         200
Ala Arg Gly Asn Leu Thr Arg Pro Pro Gly Ser Gly Glu Asp Cys Gly
         35                  40                  45

TCG GTG TCC GTG GCC TTC CCG ATC ACC ATG CTG CTG ACT GGT TTC GTG         248
Ser Val Ser Val Ala Phe Pro Ile Thr Met Leu Leu Thr Gly Phe Val
     50                  55                  60

GGC AAC GCA CTG GCC ATG CTG CTC GTG TCG CGC AGC TAC CGG CGC CGG         296
Gly Asn Ala Leu Ala Met Leu Leu Val Ser Arg Ser Tyr Arg Arg Arg
 65                  70                  75                  80

GAG AGC AAG CGC AAG AAG TCC TTC CTG CTG TGC ATC GGC TGG CTG GCG         344
Glu Ser Lys Arg Lys Lys Ser Phe Leu Leu Cys Ile Gly Trp Leu Ala
                 85                  90                  95

CTC ACC GAC CTG GTC GGG CAG CTT CTC ACC ACC CCG GTC GTC ATC GTC         392
Leu Thr Asp Leu Val Gly Gln Leu Leu Thr Thr Pro Val Val Ile Val
            100                 105                 110

GTG TAC CTG TCC AAG CAG CGT TGG GAG CAC ATC GAC CCG TCG GGG CGG         440
Val Tyr Leu Ser Lys Gln Arg Trp Glu His Ile Asp Pro Ser Gly Arg
        115                 120                 125

CTC TGC ACC TTT TTC GGG CTG ACC ATG ACT GTT TTC GGG CTC TCC TCG         488
Leu Cys Thr Phe Phe Gly Leu Thr Met Thr Val Phe Gly Leu Ser Ser
    130                 135                 140

TTG TTC ATC GCC AGC GCC ATG GCC GTC GAG CGG GCG CTG GCC ATC AGG         536
Leu Phe Ile Ala Ser Ala Met Ala Val Glu Arg Ala Leu Ala Ile Arg
145                 150                 155                 160

GCG CCG CAC TGG TAT GCG AGC CAC ATG AAG ACG CGT GCC ACC CGC GCT         584
Ala Pro His Trp Tyr Ala Ser His Met Lys Thr Arg Ala Thr Arg Ala
                165                 170                 175

GTG CTG CTC GGC GTG TGG CTG GCC GTG CTC GCC TTC GCC CTG CTG CCG         632
Val Leu Leu Gly Val Trp Leu Ala Val Leu Ala Phe Ala Leu Leu Pro
            180                 185                 190

GTG CTG GGC GTG GGC CAG TAC ACC GTC CAG TGG CCC GGG ACG TGG TGC         680
Val Leu Gly Val Gly Gln Tyr Thr Val Gln Trp Pro Gly Thr Trp Cys
        195                 200                 205

TTC ATC AGC ACC GGG CGA GGG GGC AAC GGG ACT AGC TCT TCG CAT AAC         728
Phe Ile Ser Thr Gly Arg Gly Gly Asn Gly Thr Ser Ser Ser His Asn
    210                 215                 220

TGG GGC AAC CTT TTC TTC GCC TCT GCC TTT GCC TTC CTG GGG CTC TTG         776
Trp Gly Asn Leu Phe Phe Ala Ser Ala Phe Ala Phe Leu Gly Leu Leu
225                 230                 235                 240
```

```
GCG CTG ACA GTC ACC TTT TCC TGC AAC CTG GCC ACC ATT AAG GCC CTG       824
Ala Leu Thr Val Thr Phe Ser Cys Asn Leu Ala Thr Ile Lys Ala Leu
                    245                 250                 255

GTG TCC CGC TGC CGG GCC AAG GCC ACG GCA TCT CAG TCC AGT GCC CAG       872
Val Ser Arg Cys Arg Ala Lys Ala Thr Ala Ser Gln Ser Ser Ala Gln
            260                 265                 270

TGG GGC CGC ATC ACG ACC GAG ACG GCC ATT CAG CTT ATG GGG ATC ATG       920
Trp Gly Arg Ile Thr Thr Glu Thr Ala Ile Gln Leu Met Gly Ile Met
            275                 280                 285

TGC GTG CTG TCG GTC TGC TGG TCT CCG CTC CTG ATA ATG ATG TTG AAA       968
Cys Val Leu Ser Val Cys Trp Ser Pro Leu Leu Ile Met Met Leu Lys
        290                 295                 300

ATG ATC TTC AAT CAG ACA TCA GTT GAG CAC TGC AAG ACA CAC ACG GAG      1016
Met Ile Phe Asn Gln Thr Ser Val Glu His Cys Lys Thr His Thr Glu
305                 310                 315                 320

AAG CAG AAA GAA TGC AAC TTC TTC TTA ATA GCT GTT CGC CTG GCT TCA      1064
Lys Gln Lys Glu Cys Asn Phe Phe Leu Ile Ala Val Arg Leu Ala Ser
                    325                 330                 335

CTG AAC CAG ATC TTG GAT CCT TGG GTT TAC CTG CTG TTA AGA AAG ATC      1112
Leu Asn Gln Ile Leu Asp Pro Trp Val Tyr Leu Leu Leu Arg Lys Ile
                340                 345                 350

CTT CTT CGA AAG TTT TGC CAG GTA GCA AAT GCT GTC TCC AGC TGC TCT      1160
Leu Leu Arg Lys Phe Cys Gln Val Ala Asn Ala Val Ser Ser Cys Ser
            355                 360                 365

AAT GAT GGA CAG AAA GGG CAG CCT ATC TCA TTA TCT AAT GAA ATA ATA      1208
Asn Asp Gly Gln Lys Gly Gln Pro Ile Ser Leu Ser Asn Glu Ile Ile
370                 375                 380

CAG ACA GAA GCA TGA                                                  1223
Gln Thr Glu Ala
385
```

(2) INFORMATION FOR SEQ ID NO: 6:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Glu Thr Arg Gly Tyr Gly Gly Asp Ala Pro Phe Cys Thr Arg
 1               5                  10                  15

Leu Asn His Ser Tyr Thr Gly Met Trp Ala Pro Glu Arg Ser Ala Glu
                20                  25                  30

Ala Arg Gly Asn Leu Thr Arg Pro Pro Gly Ser Gly Glu Asp Cys Gly
            35                  40                  45

Ser Val Ser Val Ala Phe Pro Ile Thr Met Leu Leu Thr Gly Phe Val
        50                  55                  60

Gly Asn Ala Leu Ala Met Leu Leu Val Ser Arg Ser Tyr Arg Arg Arg
65                  70                  75                  80

Glu Ser Lys Arg Lys Lys Ser Phe Leu Leu Cys Ile Gly Trp Leu Ala
                85                  90                  95

Leu Thr Asp Leu Val Gly Gln Leu Leu Thr Thr Pro Val Val Ile Val
            100                 105                 110

Val Tyr Leu Ser Lys Gln Arg Trp Glu His Ile Asp Pro Ser Gly Arg
        115                 120                 125

Leu Cys Thr Phe Phe Gly Leu Thr Met Thr Val Phe Gly Leu Ser Ser
        130                 135                 140
```

```
Leu Phe Ile Ala Ser Ala Met Ala Val Glu Arg Ala Leu Ala Ile Arg
145                 150                 155                 160

Ala Pro His Trp Tyr Ala Ser His Met Lys Thr Arg Ala Thr Arg Ala
                165                 170                 175

Val Leu Leu Gly Val Trp Leu Ala Val Leu Ala Phe Ala Leu Leu Pro
            180                 185                 190

Val Leu Gly Val Gly Gln Tyr Thr Val Gln Trp Pro Gly Thr Trp Cys
        195                 200                 205

Phe Ile Ser Thr Gly Arg Gly Gly Asn Gly Thr Ser Ser Ser His Asn
    210                 215                 220

Trp Gly Asn Leu Phe Phe Ala Ser Ala Phe Ala Phe Leu Gly Leu Leu
225                 230                 235                 240

Ala Leu Thr Val Thr Phe Ser Cys Asn Leu Ala Thr Ile Lys Ala Leu
                245                 250                 255

Val Ser Arg Cys Arg Ala Lys Ala Thr Ala Ser Gln Ser Ser Ala Gln
            260                 265                 270

Trp Gly Arg Ile Thr Thr Glu Thr Ala Ile Gln Leu Met Gly Ile Met
        275                 280                 285

Cys Val Leu Ser Val Cys Trp Ser Pro Leu Leu Ile Met Met Leu Lys
290                 295                 300

Met Ile Phe Asn Gln Thr Ser Val Glu His Cys Lys Thr His Thr Glu
305                 310                 315                 320

Lys Gln Lys Glu Cys Asn Phe Phe Leu Ile Ala Val Arg Leu Ala Ser
                325                 330                 335

Leu Asn Gln Ile Leu Asp Pro Trp Val Tyr Leu Leu Arg Lys Ile
            340                 345                 350

Leu Leu Arg Lys Phe Cys Gln Val Ala Asn Ala Val Ser Ser Cys Ser
        355                 360                 365

Asn Asp Gly Gln Lys Gly Gln Pro Ile Ser Leu Ser Asn Glu Ile Ile
    370                 375                 380

Gln Thr Glu Ala
385

(2) INFORMATION FOR SEQ ID NO: 7:

(i) SEQUENCE CHARACTERISTICS:
        (A) LENGTH: 1429 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 57..1151

(xi) SEQUENCE DESCRIPTION: SEQ ID NO: 7:

TGCCCCCTCC CGCTGCGGCT CTCTGGACGC CATCCCCTCC TCACCTCGAA GCCAAC         56

ATG AAG GAG ACC CGG GGC TAC GGA GGG GAT GCC CCC TTC TGC ACC CGC     104
Met Lys Glu Thr Arg Gly Tyr Gly Gly Asp Ala Pro Phe Cys Thr Arg
  1               5                  10                  15

CTC AAC CAC TCC TAC ACA GGC ATG TGG GCG CCC GAG CGT TCC GCC GAG     152
Leu Asn His Ser Tyr Thr Gly Met Trp Ala Pro Glu Arg Ser Ala Glu
             20                  25                  30
```

```
GCG CGG GGC AAC CTC ACG CGC CCT CCA GGG TCT GGC GAG GAT TGC GGA      200
Ala Arg Gly Asn Leu Thr Arg Pro Pro Gly Ser Gly Glu Asp Cys Gly
        35                  40                  45

TCG GTG TCC GTG GCC TTC CCG ATC ACC ATG CTG CTG ACT GGT TTC GTG      248
Ser Val Ser Val Ala Phe Pro Ile Thr Met Leu Leu Thr Gly Phe Val
 50                  55                  60

GGC AAC GCA CTG GCC ATG CTG CTC GTG TCG CGC AGC TAC CGG CGC CGG      296
Gly Asn Ala Leu Ala Met Leu Leu Val Ser Arg Ser Tyr Arg Arg Arg
 65                  70                  75                  80

GAG AGC AAG CGC AAG AAG TCC TTC CTG CTG TGC ATC GGC TGG CTG GCG      344
Glu Ser Lys Arg Lys Lys Ser Phe Leu Leu Cys Ile Gly Trp Leu Ala
                 85                  90                  95

CTC ACC GAC CTG GTC GGG CAG CTT CTC ACC ACC CCG GTC GTC ATC GTC      392
Leu Thr Asp Leu Val Gly Gln Leu Leu Thr Thr Pro Val Val Ile Val
            100                 105                 110

GTG TAC CTG TCC AAG CAG CGT TGG GAG CAC ATC GAC CCG TCG GGG CGG      440
Val Tyr Leu Ser Lys Gln Arg Trp Glu His Ile Asp Pro Ser Gly Arg
            115                 120                 125

CTC TGC ACC TTT TTC GGG CTG ACC ATG ACT GTT TTC GGG CTC TCC TCG      488
Leu Cys Thr Phe Phe Gly Leu Thr Met Thr Val Phe Gly Leu Ser Ser
130                 135                 140

TTG TTC ATC GCC AGC GCC ATG GCC GTC GAG CGG GCG CTG GCC ATC AGG      536
Leu Phe Ile Ala Ser Ala Met Ala Val Glu Arg Ala Leu Ala Ile Arg
145                 150                 155                 160

GCG CCG CAC TGG TAT GCG AGC CAC ATG AAG ACG CGT GCC ACC CGC GCT      584
Ala Pro His Trp Tyr Ala Ser His Met Lys Thr Arg Ala Thr Arg Ala
                165                 170                 175

GTG CTG CTC GGC GTG TGG CTG GCC GTG CTC GCC TTC GCC CTG CTG CCG      632
Val Leu Leu Gly Val Trp Leu Ala Val Leu Ala Phe Ala Leu Leu Pro
            180                 185                 190

GTG CTG GGC GTG GGC CAG TAC ACC GTC CAG TGG CCC GGG ACG TGG TGC      680
Val Leu Gly Val Gly Gln Tyr Thr Val Gln Trp Pro Gly Thr Trp Cys
            195                 200                 205

TTC ATC AGC ACC GGG CGA GGG GGC AAC GGG ACT AGC TCT TCG CAT AAC      728
Phe Ile Ser Thr Gly Arg Gly Gly Asn Gly Thr Ser Ser Ser His Asn
210                 215                 220

TGG GGC AAC CTT TTC TTC GCC TCT GCC TTT GCC TTC CTG GGG CTC TTG      776
Trp Gly Asn Leu Phe Phe Ala Ser Ala Phe Ala Phe Leu Gly Leu Leu
225                 230                 235                 240

GCG CTG ACA GTC ACC TTT TCC TGC AAC CTG GCC ACC ATT AAG GCC CTG      824
Ala Leu Thr Val Thr Phe Ser Cys Asn Leu Ala Thr Ile Lys Ala Leu
                245                 250                 255

GTG TCC CGC TGC CGG GCC AAG GCC ACG GCA TCT CAG TCC AGT GCC CAG      872
Val Ser Arg Cys Arg Ala Lys Ala Thr Ala Ser Gln Ser Ser Ala Gln
            260                 265                 270

TGG GGC CGC ATC ACG ACC GAG ACG GCC ATT CAG CTT ATG GGG ATC ATG      920
Trp Gly Arg Ile Thr Thr Glu Thr Ala Ile Gln Leu Met Gly Ile Met
            275                 280                 285

TGC GTG CTG TCG GTC TGC TGG TCT CCG CTC CTG ATA ATG ATG TTG AAA      968
Cys Val Leu Ser Val Cys Trp Ser Pro Leu Leu Ile Met Met Leu Lys
            290                 295                 300

ATG ATC TTC AAT CAG ACA TCA GTT GAG CAC TGC AAG ACA CAC ACG GAG      1016
Met Ile Phe Asn Gln Thr Ser Val Glu His Cys Lys Thr His Thr Glu
305                 310                 315                 320

AAG CAG AAA GAA TGC AAC TTC TTC TTA ATA GCT GTT CGC CTG GCT TCA      1064
Lys Gln Lys Glu Cys Asn Phe Phe Leu Ile Ala Val Arg Leu Ala Ser
                325                 330                 335

CTG AAC CAG ATC TTG GAT CCT TGG GTT TAC CTG CTG TTA AGA AAG ATC      1112
Leu Asn Gln Ile Leu Asp Pro Trp Val Tyr Leu Leu Leu Arg Lys Ile
            340                 345                 350
```

```
CTT CTT CGA AAG TTT TGC CAG GAG GAA TTT TGG GGA AAT TAAAACCTGC    1161
Leu Leu Arg Lys Phe Cys Gln Glu Glu Phe Trp Gly Asn
        355                 360                 365

CTTTCTGCCA GGATCACATC ACTGGAAGCT CCATGACTCT CTTTTTGTAA AAGAAAAAAA    1221

AATCACAGAA ACACCCACCT CCCAAACTAT TCTCTTTTAC TTCTTCCCCC AAGCCCACCC    1281

CCAAATATAA CTGTTATCCA GAAGCTGTTA TGTCCTGTTT CCATACATGT TTTTGTACTT    1341

TTACTATATC TACATACATC AATTAAACTT ATGTCCTATT GTTTTGTGAA TTTATATTTG    1401

CGTATACATT ATCGTATGTC CGGAATTC                                       1429

(2) INFORMATION FOR SEQ ID NO: 8:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO: 8:

Met Lys Glu Thr Arg Gly Tyr Gly Gly Asp Ala Pro Phe Cys Thr Arg
 1               5                  10                  15

Leu Asn His Ser Tyr Thr Gly Met Trp Ala Pro Glu Arg Ser Ala Glu
                20                  25                  30

Ala Arg Gly Asn Leu Thr Arg Pro Pro Gly Ser Gly Glu Asp Cys Gly
            35                  40                  45

Ser Val Ser Val Ala Phe Pro Ile Thr Met Leu Leu Thr Gly Phe Val
        50                  55                  60

Gly Asn Ala Leu Ala Met Leu Leu Val Ser Arg Ser Tyr Arg Arg Arg
65                  70                  75                  80

Glu Ser Lys Arg Lys Lys Ser Phe Leu Leu Cys Ile Gly Trp Leu Ala
                85                  90                  95

Leu Thr Asp Leu Val Gly Gln Leu Leu Thr Thr Pro Val Val Ile Val
                100                 105                 110

Val Tyr Leu Ser Lys Gln Arg Trp Glu His Ile Asp Pro Ser Gly Arg
            115                 120                 125

Leu Cys Thr Phe Phe Gly Leu Thr Met Thr Val Phe Gly Leu Ser Ser
        130                 135                 140

Leu Phe Ile Ala Ser Ala Met Ala Val Glu Arg Ala Leu Ala Ile Arg
145                 150                 155                 160

Ala Pro His Trp Tyr Ala Ser His Met Lys Thr Arg Ala Thr Arg Ala
                165                 170                 175

Val Leu Leu Gly Val Trp Leu Ala Val Leu Ala Phe Ala Leu Leu Pro
            180                 185                 190

Val Leu Gly Val Gly Gln Tyr Thr Val Gln Trp Pro Gly Thr Trp Cys
        195                 200                 205

Phe Ile Ser Thr Gly Arg Gly Gly Asn Gly Thr Ser Ser Ser His Asn
210                 215                 220

Trp Gly Asn Leu Phe Phe Ala Ser Ala Phe Ala Phe Leu Gly Leu Leu
225                 230                 235                 240

Ala Leu Thr Val Thr Phe Ser Cys Asn Leu Ala Thr Ile Lys Ala Leu
                245                 250                 255

Val Ser Arg Cys Arg Ala Lys Ala Thr Ala Ser Gln Ser Ser Ala Gln
            260                 265                 270

Trp Gly Arg Ile Thr Thr Glu Thr Ala Ile Gln Leu Met Gly Ile Met
```

```
                        275                 280                 285
        Cys Val Leu Ser Val Cys Trp Ser Pro Leu Leu Ile Met Met Leu Lys
            290                 295                 300
        Met Ile Phe Asn Gln Thr Ser Val Glu His Cys Lys Thr His Thr Glu
        305                 310                 315                 320
        Lys Gln Lys Glu Cys Asn Phe Phe Leu Ile Ala Val Arg Leu Ala Ser
                        325                 330                 335
        Leu Asn Gln Ile Leu Asp Pro Trp Val Tyr Leu Leu Leu Arg Lys Ile
                        340                 345                 350
        Leu Leu Arg Lys Phe Cys Gln Glu Glu Phe Trp Gly Asn
                        355                 360                 365

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: sense primer (xi) SEQUENCE DESCRIPTION: SEQ ID NO: 9:

TGGCGCTGAC AGTCACCT                                                                18

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: antisense 11

(xi) SEQUENCE DESCRIPTION: SEQ ID NO: 10:

GGCTGCCCTT TCTGTCCA                                                                18

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: antisense 19
```

(xi) SEQUENCE DESCRIPTION: SEQ ID NO: 11:

GATGTGATCC TGGCAGAA                                                    18

(2) INFORMATION FOR SEQ ID NO: 12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: antisense 27

(xi) SEQUENCE DESCRIPTION: SEQ ID NO: 12:

CAGGGAAGCA GGAATTGC                                                    18

(2) INFORMATION FOR SEQ ID NO: 13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: antisense 32

(xi) SEQUENCE DESCRIPTION: SEQ ID NO: 13:

AGGCGAAGAT TGCAGTGA                                                    18

(2) INFORMATION FOR SEQ ID NO: 14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

GATCCACCGC GGTGGAATAT TGCCCCCTCC CGCTGCGGCT CT                          42

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

GTCCAGTGGC CCGGGACGTG GTG                                                    23

(2) INFORMATION FOR SEQ ID NO: 16:

(i) SEQUENCE CHARACTERISTICS:
            (A) LENGTH: 1729 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: internal (ix) FEATURE:
            (A) NAME/KEY: CDS
            (B) LOCATION: 57..1229

(xi) SEQUENCE DESCRIPTION: SEQ ID NO: 16:

```
TGCCCCCTCC CGCTGCGGCT CTCTGGACGC CATCCCCTCC TCACCTCGAA GCCAAC            56

ATG AAG GAG ACC CGG GGC TAC GGA GGG GAT GCC CCC TTC TGC ACC CGC         104
Met Lys Glu Thr Arg Gly Tyr Gly Gly Asp Ala Pro Phe Cys Thr Arg
 1               5                  10                  15

CTC AAC CAC TCC TAC ACA GGC ATG TGG GCG CCC GAG CGT TCC GCC GAG         152
Leu Asn His Ser Tyr Thr Gly Met Trp Ala Pro Glu Arg Ser Ala Glu
                20                  25                  30

GCG CGG GGC AAC CTC ACG CGC CCT CCA GGG TCT GGC GAG GAT TGC GGA         200
Ala Arg Gly Asn Leu Thr Arg Pro Pro Gly Ser Gly Glu Asp Cys Gly
            35                  40                  45

TCG GTG TCC GTG GCC TTC CCG ATC ACC ATG CTG CTG ACT GGT TTC GTG         248
Ser Val Ser Val Ala Phe Pro Ile Thr Met Leu Leu Thr Gly Phe Val
        50                  55                  60

GGC AAC GCA CTG GCC ATG CTG CTC GTG TCG CGC AGC TAC CGG CGC CGG         296
Gly Asn Ala Leu Ala Met Leu Leu Val Ser Arg Ser Tyr Arg Arg Arg
 65                  70                  75                  80

GAG AGC AAG CGC AAG AAG TCC TTC CTG CTG TGC ATC GGC TGG CTG GCG         344
Glu Ser Lys Arg Lys Lys Ser Phe Leu Leu Cys Ile Gly Trp Leu Ala
                85                  90                  95

CTC ACC GAC CTG GTC GGG CAG CTT CTC ACC ACC CCG GTC GTC ATC GTC         392
Leu Thr Asp Leu Val Gly Gln Leu Leu Thr Thr Pro Val Val Ile Val
                100                 105                 110

GTG TAC CTG TCC AAG CAG CGT TGG GAG CAC ATC GAC CCG TCG GGG CGG         440
Val Tyr Leu Ser Lys Gln Arg Trp Glu His Ile Asp Pro Ser Gly Arg
            115                 120                 125

CTC TGC ACC TTT TTC GGG CTG ACC ATG ACT GTT TTC GGG CTC TCC TCG         488
Leu Cys Thr Phe Phe Gly Leu Thr Met Thr Val Phe Gly Leu Ser Ser
        130                 135                 140

TTG TTC ATC GCC AGC GCC ATG GCC GTC GAG CGG GCG CTG GCC ATC AGG         536
Leu Phe Ile Ala Ser Ala Met Ala Val Glu Arg Ala Leu Ala Ile Arg
145                 150                 155                 160

GCG CCG CAC TGG TAT GCG AGC CAC ATG AAG ACG CGT GCC ACC CGC GCT         584
Ala Pro His Trp Tyr Ala Ser His Met Lys Thr Arg Ala Thr Arg Ala
                165                 170                 175

GTG CTG CTC GGC GTG TGG CTG GCC GTG CTC GCC TTC GCC CTG CTG CCG         632
Val Leu Leu Gly Val Trp Leu Ala Val Leu Ala Phe Ala Leu Leu Pro
                180                 185                 190
```

```
GTG CTG GGC GTG GGC CAG TAC ACC GTC CAG TGG CCC GGG ACG TGG TGC        680
Val Leu Gly Val Gly Gln Tyr Thr Val Gln Trp Pro Gly Thr Trp Cys
            195                 200                 205

TTC ATC AGC ACC GGG CGA GGG GGC AAC GGG ACT AGC TCT TCG CAT AAC        728
Phe Ile Ser Thr Gly Arg Gly Gly Asn Gly Thr Ser Ser Ser His Asn
        210                 215                 220

TGG GGC AAC CTT TTC TTC GCC TCT GCC TTT GCC TTC CTG GGG CTC TTG        776
Trp Gly Asn Leu Phe Phe Ala Ser Ala Phe Ala Phe Leu Gly Leu Leu
225                 230                 235                 240

GCG CTG ACA GTC ACC TTT TCC TGC AAC CTG GCC ACC ATT AAG GCC CTG        824
Ala Leu Thr Val Thr Phe Ser Cys Asn Leu Ala Thr Ile Lys Ala Leu
                245                 250                 255

GTG TCC CGC TGC CGG GCC AAG GCC ACG GCA TCT CAG TCC AGT GCC CAG        872
Val Ser Arg Cys Arg Ala Lys Ala Thr Ala Ser Gln Ser Ser Ala Gln
            260                 265                 270

TGG GGC CGC ATC ACG ACC GAG ACG GCC ATT CAG CTT ATG GGG ATC ATG        920
Trp Gly Arg Ile Thr Thr Glu Thr Ala Ile Gln Leu Met Gly Ile Met
        275                 280                 285

TGC GTG CTG TCG GTC TGC TGG TCT CCG CTC CTG ATA ATG ATG TTG AAA        968
Cys Val Leu Ser Val Cys Trp Ser Pro Leu Leu Ile Met Met Leu Lys
    290                 295                 300

ATG ATC TTC AAT CAG ACA TCA GTT GAG CAC TGC AAG ACA CAC ACG GAG       1016
Met Ile Phe Asn Gln Thr Ser Val Glu His Cys Lys Thr His Thr Glu
305                 310                 315                 320

AAG CAG AAA GAA TGC AAC TTC TTC TTA ATA GCT GTT CGC CTG GCT TCA       1064
Lys Gln Lys Glu Cys Asn Phe Phe Leu Ile Ala Val Arg Leu Ala Ser
                325                 330                 335

CTG AAC CAG ATC TTG GAT CCT TGG GTT TAC CTG CTG TTA AGA AAG ATC       1112
Leu Asn Gln Ile Leu Asp Pro Trp Val Tyr Leu Leu Leu Arg Lys Ile
            340                 345                 350

CTT CTT CGA AAG TTT TGC CAG ATC AGG TAC CAC ACA AAC AAC TAT GCA       1160
Leu Leu Arg Lys Phe Cys Gln Ile Arg Tyr His Thr Asn Asn Tyr Ala
        355                 360                 365

TCC AGC TCC ACC TCC TTA CCC TGC CAG TGT TCC TCA ACC TTG ATG TGG       1208
Ser Ser Ser Thr Ser Leu Pro Cys Gln Cys Ser Ser Thr Leu Met Trp
    370                 375                 380

AGC GAC CAT TTG GAA AGA TAATGAAAGA ACGGAGTTGG ACATTTTATT              1256
Ser Asp His Leu Glu Arg
385                 390

GCAATTCCTG CTTCCCTGAA TTTGCATATT TCTTCCCACC TGAGAAGGAT AATTATATAT     1316

TTTAATTTGG ATTATTTCTT CATTTTTATC TTTTTATTTT AATGATTGTT TTGTCAGTAA     1376

TACCCATGGA GATCAACTTT ATTATTATAA TCCATGCCTC TGAATATTAG ATTGGTTTCT     1436

TGGATGGGAT TTTGATATGC ATTTAAGAAG TTGGGAAGAA TTTCACAGAT GATGATTGGA     1496

GGAAAAGTGA TGAAAAGAAG ACCTGTGTTC CAGGAGTTTT CTCCAACTTC AAACCTTTAC     1556

GTGAATCTTA ACCAAAGTGA CATCTTTACA TTTCATGATA GCTTGCTTTT GCAATATGAG     1616

TTTGAAAAAT CAAGATAAGC TTATGATGGT GAAAAGTCAA CATATTGAGA GTGATAATTC     1676

AATTAATAGG ATATGAACTT AACGACATAT AAAAGCAAAT GAGGGCAGGA GGG            1729
```

(2) INFORMATION FOR SEQ ID NO: 17:

(i) SEQUENCE CHARACTERISTICS:
        (A) LENGTH: 390 amino acids
        (B) TYPE: amino acid
        (D) TOPOLOGY: linear (ii) MOLECULE TYPE: protein (xi) SEQUENCE DESCRIPTION: SEQ ID NO: 17:

```
Met Lys Glu Thr Arg Gly Tyr Gly Gly Asp Ala Pro Phe Cys Thr Arg
 1               5                  10                  15

Leu Asn His Ser Tyr Thr Gly Met Trp Ala Pro Asp Gly Ser Ala Glu
                20                  25                  30

Ala Arg Gly Asn Leu Thr Arg Pro Pro Gly Ser Gly Glu Asp Cys Gly
            35                  40                  45

Ser Val Ser Val Ala Phe Pro Ile Thr Met Leu Leu Thr Gly Phe Val
        50                  55                  60

Gly Asn Ala Leu Ala Met Leu Leu Val Ser Arg Ser Tyr Arg Arg Arg
 65                 70                  75                  80

Glu Ser Lys Arg Lys Lys Ser Phe Leu Leu Cys Ile Gly Trp Leu Ala
                85                  90                  95

Leu Thr Asp Leu Val Gly Gln Leu Leu Thr Thr Pro Val Val Ile Val
                100                 105                 110

Val Tyr Leu Ser Lys Gln Arg Trp Glu His Ile Asp Pro Ser Gly Arg
            115                 120                 125

Leu Cys Thr Phe Phe Gly Leu Thr Met Thr Val Phe Gly Leu Ser Ser
    130                 135                 140

Leu Phe Ile Ala Ser Ala Met Ala Val Glu Arg Ala Leu Ala Ile Arg
145                 150                 155                 160

Ala Pro His Trp Tyr Ala Ser His Met Lys Thr Arg Ala Thr Arg Ala
                165                 170                 175

Val Leu Leu Gly Val Trp Leu Ala Val Leu Ala Phe Ala Leu Leu Pro
            180                 185                 190

Val Leu Gly Val Gly Gln Tyr Thr Val Gln Trp Pro Gly Thr Trp Cys
        195                 200                 205

Phe Ile Ser Thr Gly Arg Gly Gly Asn Gly Thr Ser Ser Ser His Asn
    210                 215                 220

Trp Gly Asn Leu Phe Phe Ala Ser Ala Phe Ala Phe Leu Gly Leu Leu
225                 230                 235                 240

Ala Leu Thr Val Thr Phe Ser Cys Asn Leu Ala Thr Ile Lys Ala Leu
                245                 250                 255

Val Ser Arg Cys Arg Ala Lys Ala Thr Ala Ser Gln Ser Ser Ala Gln
            260                 265                 270

Trp Gly Arg Ile Thr Thr Glu Thr Ala Ile Gln Leu Met Gly Ile Met
        275                 280                 285

Cys Val Leu Ser Val Cys Trp Ser Pro Leu Leu Ile Met Met Leu Lys
    290                 295                 300

Met Ile Phe Asn Gln Thr Ser Val Glu His Cys Lys Thr His Thr Glu
305                 310                 315                 320

Lys Gln Lys Glu Cys Asn Phe Phe Leu Ile Ala Val Arg Leu Ala Ser
                325                 330                 335

Leu Asn Gln Ile Leu Asp Pro Trp Val Tyr Leu Leu Leu Arg Lys Ile
            340                 345                 350

Leu Leu Arg Lys Phe Cys Gln Ile Arg Tyr His Thr Asn Asn Tyr Ala
        355                 360                 365

Ser Ser Ser Thr Ser Leu Pro Cys Gln Cys Ser Ser Thr Leu Met Trp
    370                 375                 380

Ser Asp His Leu Glu Arg
385                 390
```

HUMAN EP$_3$ PROSTAGLANDIN RECEPTOR

This is a divisional application of Ser. No. 09/363,783, now U.S. Pat. No. 6,197,933 filed on Jul. 29, 1999, which was a divisional of application Ser. No. 08/155,055, filed Nov. 19, 1993, now U.S. Pat. No. 6,057,433, which applications are hereby incorporated by reference herein.

FIELD OF THE INVENTION

This invention relates to the cloning and expression of the human EP$_3$ prostaglandin receptor. Methods of identifying compounds capable of both binding to and activating the human EP$_3$ receptor are also disclosed.

BACKGROUND OF THE INVENTION

Prostaglandins are a group of lipid-soluble hormone mediators derived from the metabolism of arachidonic acid via the cyclooxygenase enzymatic pathway. In the prostaglandin biosynthetic pathway, arachidonic acid is first converted to the endoperoxide PGH2 by PGH2 synthases followed by the cell-specific isomerization or reduction of PGH2 to the active prostaglandins: PGD$_2$, PGE$_2$, PGF$_{2\alpha}$, prostacyclin (PGI$_2$) and thromboxane (TxA$_2$). Following enzymatic conversion, prostaglandins exert their actions locally on the cells in which they were synthesized (autocrine) and/or on nearby cells (paracrine) through specific G protein-coupled receptors (Smith, (1992) *Am. J. Physiol.*, 263: F181–F191) to either stimulate or inhibit the production of second messengers. Prostaglandins elicit a diverse spectrum of often opposing biological effects including muscle contraction and relaxation, platelet aggregation, vasodilation and inflammation.

PGE$_2$ exhibits a broad range of actions in a number of tissues by binding to at least three EP receptor subtypes. It acts through pharmacologically distinct stimulatory (EP$_2$) and inhibitory (EP3) PGE receptor subtypes to stimulate and inhibit cAMP formation, respectively (Sonnenburg, and Smith, (1988) *J. Biol. Chem.*, 263: 6155–6160). PGE$_2$ also stimulates calcium release and protein kinase C activity in the rabbit kidney collecting tubule, most likely by binding to the EP$_1$ receptor subtype that is coupled to stimulation of phospholipase C (Hebert et al., (1990) *Am. J. Physiol.*, 259: F318–F325). The EP$_3$ receptor subtype is involved in inhibition of gastric acid secretion, modulation of neurotransmitter release, inhibition of sodium and water reabsorption in the kidney tubule, potentiation of platelet aggregation at low concentrations (below 1 µM) and inhibition of platelet aggregation at higher concentrations (Tynan et al., (1984) Prostaglandins, 27: 683–696; Matthews and Jones, (1993) *British J. Pharmacol.*, 108: 363–369).

Development of therapeutic prostaglandins requires selective action at receptor subtypes. The murine EP$_2$ and EP$_3$ prostaglandin receptors have been cloned and sequenced (Honda et al., (1993) *J. Biol. Chem* ., 268: 7759–7762; Sugimoto et al., (1992) *J. Biol. Chem.*, 267: 6463–6466). The deduced protein sequences indicate that both are members of the G protein-linked receptor superfamily, having seven putative membrane-spanning hydrophobic domains. The proteins share significant amino acid sequence similarity with other members of this family including the thromboxane (TP) receptor (Hirata et al., (1991) *Nature* 349: 617–620), rhodopsin and the adrenergic receptors. In order to characterize the pharmacology of the murine EP$_3$ receptor, the gene was transfected into COS-7 cells which lack the EP$_3$ receptor and competition binding assays using tritiated PGE$_2$ were performed on the plasma membrane fraction (Sugimoto et al., (1992) *J. Biol. Chem.*, 267: 6463–6466).

However, these results only addressed the binding of compounds to the murine receptors. There is still the need to identify compounds which specifically bind to the human EP$_3$ receptor, since the pharmacology of rodent G-protein coupled receptors does not always match their human homologs (Oksenberg et al., (1992) *Nature*, 360: 161–163; Link et al., (1992) *Mol. Pharmacol.*, 42: 16–27).

SUMMARY OF THE INVENTION

One embodiment of the present invention is an isolated DNA molecule encoding the human prostaglandin EP$_3$ receptor. Preferably, this molecule has the nucleotide sequence of SEQ ID NOS: 3, 5, 7 or 16.

Another embodiment of the present invention is an isolated, unique 18 nucleotide DNA sequence contained within SEQ ID NOS: 3, 5, 7 or 16.

A further embodiment of the present invention are the proteins derived from the aforementioned DNA sequences.

The present invention also embodies a vector containing SEQ ID NOS: 3, 5, 7 or 16 operably linked to a heterologous promoter.

Another aspect of the present invention provides isolated antibodies directed to the human EP$_3$ receptor protein. Preferably, these antibodies are polyclonal; most preferably, these antibodies are monoclonal.

A further embodiment consists of a method of screening compounds for binding to the human EP$_3$ receptor by the following steps:

transfecting cells with a DNA molecule encoding a human EP$_3$ receptor operably linked to a promoter;

culturing the cells to express the human EP$_3$ receptor;

incubating the cultured cells in the presence of a labeled compound to be tested for binding affinity to the human EP$_3$ receptor; and measuring the amount of label bound to the cells.

Preferably, the cell line is COS-7, the human EP$_3$ receptor is encoded by the polynucleotide of SEQ ID NOS: 3, 5, 7, or 16, and the expression vector is mammalian. Most preferably, the mammalian expression vector is pBC12BI. Additionally, the compound of interest may advantageously be either radiolabeled, colorimetrically labeled or fluorimetrically labeled. In another aspect of this preferred embodiment, prior to the incubation step, cell membranes containing the expressed human EP$_3$ receptor are isolated.

Still another embodiment of the present invention is a method of determining the ability of a compound to inhibit ligand binding to the human EP$_3$ receptor by the steps of:

transfecting cells with a DNA sequence encoding the human EP$_3$ receptor operably linked to a promoter;

culturing the cells to express the human EP$_3$ receptor;

incubating the cultured cells in the presence of a labeled ligand having binding affinity for the receptor and a test compound; and determining the level of binding of the ligand to the expressed human EP$_3$ receptor, wherein a lower level of ligand binding in the presence of the compound indicates that the compound binds to the receptor.

Preferably, the cell line is COS-7. Advantageously, the compound may be either radioactively, colorimetrically or fluorimetrically labeled. Alternatively, the ligand may be labeled. Most preferably, the expression vector is pBC12BI and the ligand is PGE$_2$. In another aspect of this preferred embodiment, prior to the incubation step, cell membranes containing the expressed human $EP_3$ receptor are isolated.

Another aspect of the present invention provides a method for identifying compounds that are receptor agonists by the following steps:

transfecting cells with the human $EP_3$ receptor gene operably linked to a promoter;

transfecting cells with a DNA segment encoding cyclic AMP-responsive chloramphenicol acetyltransferase (CAT);

incubating the cells in the presence or absence of an activator of adenylate cyclase and in the presence of a compound to be tested; and assaying the amount of CAT produced, where a change in CAT activity indicates that the compound is an agonist of the receptor.

Preferably, the cell line is mammalian; most preferably, the mammalian cells are JEG-3 choriocarcinoma cells, and the activator of adenylate cyclase is forskolin.

The present invention further provides a cell line in continuous culture expressing the human $EP_3$ receptor encoded by the DNA of SEQ ID NOS: 3, 5, 7 or 16. Preferably these cells are CHO cells.

DETAILED DESCRIPTION OF THE INVENTION

Figure 1:
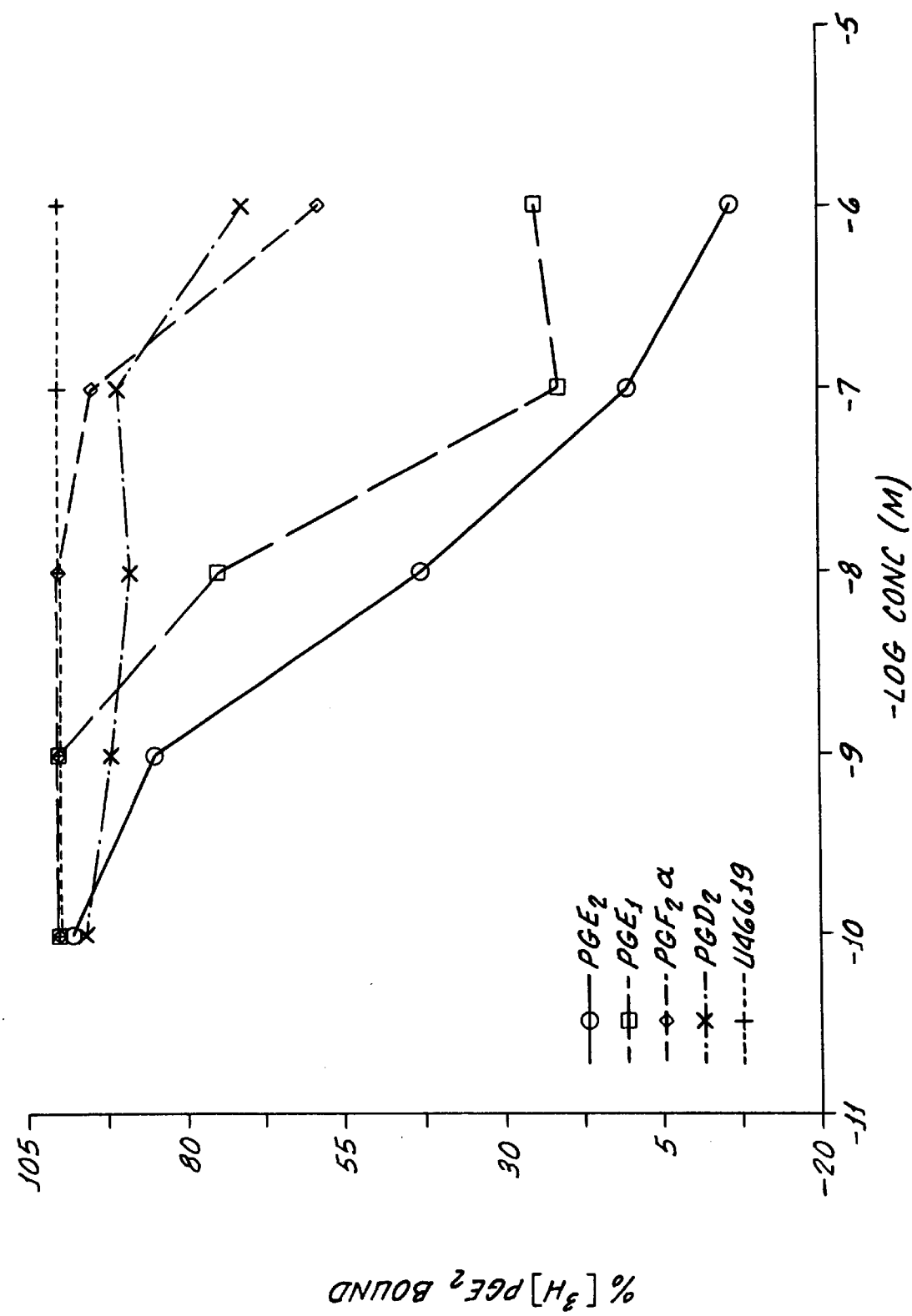
FIG. 1 illustrates a competition curve of [$^3$H]PGE$_2$ binding to membranes from COS-7 cells transfected with the full-length $hEP_3$27 receptor. The y-axis indicates the percentage of [$^3$H]PGE$_2$ specifically bound and the x-axis indicates the concentration of competitor added (-log M).

This invention discloses the cloning, sequencing and characterization of the human $EP_3$ ($hEP_3$) prostaglandin receptor. The human $EP_3$ gene sequence, fragments thereof, vectors containing this sequence or unique fragments thereof, cells transfected with this sequence or fragments thereof and protein purified from these cells will be useful for studying the pharmacology and the cellular distribution and expression of the human $EP_3$ receptor.

Unexpectedly, three alternatively spliced variants of the human $EP_3$ receptor were identified by hybridization screening of a human small intestine cDNA library. The existence of corresponding variant mRNAs has been verified by reverse transcriptase PCR. The existence of these splice variants was unexpected since only a single variant that results from an internal deletion has been described for the mouse receptor. Since the sequence differences occur in the carboxy-terminal regions, this may be important in receptor-effector coupling.

Fragments of the $hEP_3$ receptor gene consisting of at least 18 consecutive nucleotides unique to $hEP_3$ will be useful as PCR probes for isolating other human prostaglandin receptors as well as the corresponding receptor gene from other species. These oligonucleotides will be useful for in situ hybridization and to probe Northern blots of RNA isolated from various tissues by well known methods to determine the $hEP_3$ receptor distribution.

As specific subsets of the prostaglandin receptor family may be involved in different cellular actions, it is important to identify the receptor subtypes expressed by each cell. It can be appreciated that those of ordinary skill in the art could determine unique fragments of the human $EP_3$ receptor and use these fragments as probes to determine cells expressing one of the prostaglandin receptor genes.

In addition, DNA sequences of 18 nucleotides correspond to six amino acids. Those of ordinary skill in the art will appreciate that a six amino acid peptide, when coupled to an immunogenic carrier protein such as keyhole limpet hemocyanin, can be utilized as an antigen to raise antibodies against $hEP_3$ receptor epitopes. Alternatively, the $hEP_3$ cDNA or fragments thereof can be expressed and the resulting polypeptide recovered and used as an immunogen. Antibodies against the $hEP_3$ receptor protein will allow immunohisto-chemical localization of the protein in cells, tissues and body fluids, thereby providing a means for identification of cells expressing the $hEP_3$ receptor subtype.

The use of a number of eukaryotic expression vectors is within the scope of the present invention. Those of ordinary skill in the art will appreciate that once the $hEP_3$ receptor clone has been identified and sequenced, it can rapidly be incorporated into almost any desired vector. In the present invention, the most preferable expression vectors are mammalian, with the most preferable the vector being pBC12BI. The incorporation of the alternatively spliced $hEP_3$ variant DNA sequences into expression vectors, and their subsequent transfection and expression in mammalian cells, is also envisioned. In addition, the use of yeast, baculovirus and prokaryotic expression vectors is also within the scope of the present invention as is the production of the $hEP_3$ receptor or fragments thereof in these cell types.

Assays using the expressed protein, either in whole transfected cells or in membrane preparations, will be particularly useful in the identification of $hEP_3$ receptor agonists and antagonists and may aid in the identification of pharmacologically relevant compounds. The binding of compounds to cells expressing the receptor can then be determined. Although the preferred method of identifying receptor ligands is by radiolabeling, other methods known in the art are also within the scope of the present invention. For instance, well known methods exist for colorimetrically and fluorimetrically labeling compounds. One can also measure functional responses in cells expressing the $hEP_3$ receptor protein by using signaling systems including, but not limited to, adenylate cyclase, phosphoinositide hydrolysis, guanylate cyclase, ion fluxes and pH changes. Although JEG-3 choriocarcinoma cells were used, the use of other cell types amenable to such analysis is also contemplated. The response systems are either present in the host cell or can be introduced into the host cell along with the receptor. Although in the present invention the transfected cells were mammalian, any cell type able to express a transfected $hEP_3$ gene is within the scope of the present invention. Although transient transfection of cells has been described, production of stable transfectants expressing the $hEP_3$ gene using well-known methods is also contemplated.

With the gene sequence determined, mutations can now be introduced in order to study structure-function relationships as they relate to ligand binding and effector system coupling. This receptor was found to have seven putative hydrophobic membrane-spanning domains and is thus believed to be a member of the G protein-coupled receptor superfamily. The cloning of the $hEP_3$ receptor gene and analysis of the expressed protein will help differentiate the functions of EP receptor subtypes. As a first step of isolating the $hEP_3$ receptor gene, PCR amplification of human small intestine mRNA was performed as discussed in the following example.

EXAMPLE 1

Cloning of a Human $EP_3$ Receptor Fragment by PCR

Sense and antisense primers corresponding to the first extracellular loop and the sixth transmembrane domain, respectively, of the murine $EP_3$ receptor were used in a PCR reaction to amplify corresponding sequences in total RNA from human small intestine (Clontech). The sense and antisense primers used for cloning a human $EP_3$ receptor sequence were designed from nucleotides 301–326 (SEQ ID NO: 1) and 775–797 (SEQ ID NO: 2), respectively, of the mouse $EP_3$ receptor sequence (Sugimoto et al., (1992) *J. Biol. Chem.*, 267: 6463–6466).
5'-GA(T/C)CCGTCG(T/G)GICGICTITG(C/T)(C/A)(C/G)ITT-3' (SEQ ID NO:1)
5'-AC(A/G)CACATIAT(A/T/G/C)CCCAT(A/T/G/C)A(A/G)(T/C)TG-3' (SEQ ID NO:2)

The primers were added to a combined reverse transcription/PCR reaction. The reverse transcription reaction contained 14 µl 10×PCR buffer (Perkin-Elmer, Norwalk, Conn.), 3.5 µl Rnasin (Boehringer Mannheim, Indianapolis, Ind.; 40 units/µ), 35 µl dNTPs (5 mM), 7 µl random primers (1 µg/µl), 14 µl RNA (1 µg/µl) and 7 µl AMV reverse transcriptase (Boehringer Mannheim, 25 units/µl) in a final volume of 140 µl. The samples were incubated at room temperature (22° C.) for 10 min, 42° C. for 1 hour, 95° C. for 5 min and placed on ice. The PCR reaction was performed using 20 µl of the reverse transcription reaction, 3 µl 10×PCR buffer, 5 µl dimethyl sulfoxide (DMSO), 5 µl sense primer (20 µM), 5 µl antisense primer (20 µM) and 1 µl Taq polymerase (Perkin-Elmer, 2.5 units/µl) in a final volume of 50 µl under the following conditions: 94° C., 3 min; 50° C., 2 min; 72° C., 3 min; 59 cycles of 94° C., 1 min; 50° C., 2 min; 72° C., 3 min; and a final cycle of 72° C., 15 min; 4° C., 12 hours.

A 15 µl sample of the PCR reaction was analyzed by electrophoresis on a 1% agarose gel and stained with ethidium bromide. A single 500 base pair fragment was obtained which is in the expected size range as deduced from the murine $EP_3$ receptor sequence. The band was purified using Geneclean® (Bio 101, Inc., La Jolla, Calif.) and cloned into pBluescript® using a G/C tailing reaction according to the manufacturer's instructions (Boehringer Mannheim). The samples were used to transform *E. coli* DH10B cells by electroporation. A positive clone ($B_1$) was isolated and its sequence then determined using ΔTaq-PCR sequencing according to the manufacturer's instructions (United States Biochemical, Cleveland, Ohio). The $hEP_3$ sequence exhibited significant similarity with the murine $EP_3$ receptor sequence.

To isolate a genomic clone corresponding to the $B_1$ cDNA, a lambda genomic library was screened with the $B_1$ clone as described in the following example.

EXAMPLE 2

Isolation of a Genomic $EP_3$ Receptor Clone

A human genomic DNA library in λFix II (Stratagene, La Jolla, Calif.) was screened by plaque hybridization analysis (Sambrook et al., (1989) in Molecular Cloning: a Laboratory Manual, Cold Spring Harbor Laboratory) using a $^{32}P$ labeled $B_1$ probe as described in Example 1. Nitrocellulose filters were placed over 22 petri dishes having a total of approximately $4.4 \times 10^5$ recombinant clones to lift the plaque DNA. The DNA was denatured, neutralized and baked for 2 hours at 80° C. The filters were prehybridized for 2 hours at 37° C. in 50% formamide, 1 M NaCl, 1% SDS, 100 µg/ml herring sperm DNA to block nonspecific binding, then hybridized with the $B_1$ probe overnight at 37° C. The $B_1$ probe was labeled by well known methods with $^{32}P$ using a DNA nick-translation kit (Gibco/BRL) to a concentration of $5 \times 10^6$ dpm/ml. The filters were washed for 1 hour at 37° C. in 2×SSC, 0.1 SDS and then for 1 hour at 53° C. in 0.1×SSC, 0.1% SDS. The second wash, performed under more stringent conditions (less salt and higher temperature) removed more nonspecific binding. The filters were analyzed by autoradiography and a positive clone was isolated ($EP_3\lambda 12$) after two additional plaque hybridization rounds.

DNA was prepared from plate lysates of the positive clone ($EP_3\lambda 12$) using LambdaSorb® (Promega, Madison, Wis.). The DNA was digested with EcoRI and a 13 kb insert was obtained. Further restriction analysis and Southern blotting produced a 2.4 kb BamHI fragment that hybridized with the $^{32}P$-labeled $B_1$ clone. This 2.4 kb fragment was cloned into pBluescript® and a series of nested deletions was made with the Erase-A-Base® system (Promega). Five overlapping deletion clones were sequenced by the Sequenase® deaza-7-dGTP protocol (United States Biochemical).

As indicated by DNA sequence analysis, an open reading frame was present within this sequence which, when translated, shared greater than 80% identity with the mouse $EP_3$ receptor sequence. The amino terminus of the deduced amino acid sequence of the open reading frame started in approximately the same region as that of the mouse $EP_3$ amino terminus, but the carboxy terminus of the human sequence ended at a point equivalent to the putative sixth transmembrane domain of the mouse $EP_3$ receptor. Examination of the nucleotide sequence in this region of the human genomic clone was consistent with an intron/exon boundary suggesting the presence of an intron. Southern blot analysis of the full length $EP_3\lambda 12$ insert with a probe encoding the seventh transmembrane domain from a subsequently characterized $hEP_3$ receptor cDNA was negative, indicating that the downstream exon(s) were not present in this genomic clone.

To isolate a longer $hEP_3$ receptor cDNA clone, a human small intestine cDNA library was screened with the $B_1$ probe as discussed in the following example:

EXAMPLE 3

Isolation of $EP_3$ Receptor cDNA Clones

A human small intestine cDNA library (Clontech) in λgt10 was screened with the $^{32}P$ labelled $B_1$ PCR product as in Example 2. Approximately 860,000 recombinants were screened resulting in two positive clones ($hEP_3$27 and $hEP_3$32). These clones were subcloned into the EcoRI site of pBluescript and sequenced as described above. However, neither clone contained a complete open reading frame. Another 460,000 recombinants were screened under the same conditions except that the filters were washed for 1 hour at 50° C. in 1×SSC, 0.1% SDS. Four positive clones were obtained ($hEP_3$1, $hEP_3$4, $hEP_3$19, $hEP_3$21), subcloned and sequenced.

Although none of the isolated cDNA clones was full length, an alignment of the entire open reading frame could be determined by matching overlapping sequenced gene regions. In a third screen, 500,000 recombinants were screened with a $^{32}$P-labeled RNA probe generated from one of the nested deletion genomic clones that ends upstream of the intron. Filters were prehybridized, then hybridized with approximately 2×10$^6$ dpm/ml at 60° C. in 6×SSC, 20 mM sodium phosphate, pH 7.6, 1×Denhardt's solution, 1 mM dithiothreitol, and 100 μg/ml poly A RNA. The filters were washed under increasingly stringent conditions with a final wash in 0.1×SSC, 0.1% SDS at 60° C. for 20 minutes. A single full-length cDNA clone was identified (EP$_3$11.2), confirming the previously sequenced overlapping reading frames. In addition, there was evidence for three alternative splicing variants in the 3' regions of the human cDNAs since three of the clones obtained encoding this region had different nucleotide sequences from hEP$_3$27. These variants were called hEP$_3$32, hEP$_3$11.2 and hEP$_3$19 (SEQ ID NOS: 3, 5, and 7, respectively). A schematic diagram indicating the alternatively spliced 3' regions is shown in FIG. 1. hEP$_3$27, hEP$_3$11.2 and hEP$_3$19 differed from one another in the deduced amino acid sequence of their carboxy termini which diverged at the same point (nucleotide 1133 of SEQ ID NO: 16). hEP$_3$32 shared amino acid identity in its carboxy terminal region with hEP$_3$27 and the mouse EP$_3$α receptor, but had a completely different 3' untranslated sequence. To confirm the presence of mRNAs encoding the hEP$_3$ receptor variants, PCR amplification of the region spanning the divergent point was performed as described below.

EXAMPLE 4

PCR Cloning of Splice Variants

Sense and antisense primers that span the diverged point were chosen to amplify sequences specific for each variant. The sense primer (5'-TGGCGCTGACAGTCACCT; SEQ ID NO: 9) was common to all hEP$_3$ receptor clones and annealed at nucleotides 774–791 of SEQ. ID NO. 16. The antisense primers were specific to the unique 3'-untranslated regions of the clones as follows:

|  |  |  | Nucleotide # | SEQ ID |
|---|---|---|---|---|
| antisense | 11 | 5'-GGCTGCCCTTTCTGTCCA-3' | 1166-1183 | 10 |
| antisense | 19 | 5'-GATGTGATCCTGGCAGAA-3' | 1164-1181 | 11 |
| antisense | 27 | 5'-CAGGGAAGCAGGAATTGC-3' | 1257-1274 | 12 |
| antisense | 32 | 5'-AGGCGAAGATTGCAGTGA-3' | 1356-1373 | 13 |

The reverse transcription reactions contained 23 μl water, 2 μl RNase inhibitor (50 units/μ, Boehringer Mannheim), 2 μl denatured total RNA (1 μg/μl), 6 μl 10×buffer (Boehringer Mannheim), 12 μl MgCl$_2$ (25 mM), 6 μl dNTPs (10 mM each), 6 μl poly (dN)$_6$ (0.04 A$_{260}$/μl) or 6 μl poly (dT)$_{15}$ (0.02 A$_{260}$/μl), 0.6 μl acetylated BSA (10 mg/ml, Promega), 2.4 μl AMV reverse transcriptase (25 units/μl, Boehringer Mannheim) in a final volume of 60 μl. The reactions were incubated at room temperature for 10 min, 42° C. for 45 min, 95° C. for 5 min and held on ice.

The PCR reactions contained 4 μl of the reverse transcription reaction, 33.5 μl water, 5 μl 10×buffer (Perkin-Elmer), 3 μl MgCl$_2$, 2 μl dNTPs (1.25 mM each), 1 μl TMA (2.5×10$^{-3}$ mM), 0.625 μl sense primer (25 μM), 0.25 μl Taq polymerase (Perkin-Elmer, 5 units/μl ) in a final volume of 50 μl. There was an initial denaturation step of 94° C. for 2 min, 35 cycles at 94° C. for 15 sec, 60° C. for 15 sec and 72° C. for 36 sec. Finally, there was a single 72° C., 6 min incubation. Half of the PCR reactions (25 μl) was analyzed by electrophoresis on a 1.5% agarose gel stained with ethidium bromide. These samples were run in parallel with positive controls (plasmid DNA with template) and negative controls (plasmid DNA without template).

Fragments of the predicted size (hEP$_3$11: 409 bp; hEP$_3$19: 407 bp; hEP$_3$27: 500 bp; hEP$_3$32: 599 bp) were amplified with RNA from human small intestine, heart, pancreas, and ocular ciliary muscle, confirming the presence of all of the hEP$_3$ receptor variants described above. Interestingly, PCR using primers specific for variant hEP$_3$19 on human small intestine RNA produced a second fragment 50–100 base pairs larger than would be expected. This could represent an additional variant that has an insertion in the carboxy terminal region of hEP$_3$19. Since this second fragment was not observed in PCR of RNA isolated from other tissues, this may represent a tissue-specific variant.

The difference between the 3' splice variants of the present invention and those of the murine receptor (Sugimoto et al., (1993) J. Biol. Chem., 268: 2712–2718) is that the human amino acid (and 3' untranslated nucleotide) sequences are all different, whereas the murine variant arises by a deletion of an 89 base pair sequence. This creates another reading frame downstream from this junction which extends the coding region to a new stop codon 77 base pairs downstream from the original stop codon. As a consequence, a 30 amino acid sequence is replaced with a 26 amino acid sequence. The variants of the present invention, however, arise by a completely different, presently unknown, mechanism.

As mentioned previously, the differences in amino acid sequence at the carboxy termini of these variants may be significant in the regulation and functional coupling of these receptor isoforms to effector molecules. The different carboxy-terminal regions may either interact with different protein effectors thus initiating different enzymatic cascades, may change the efficiency of coupling to the same effector system or may differentially regulate coupling by changes in phosphorylation states. The hEP$_3$19 receptor variant, which has only 6 amino acids at its carboxy terminus, lacks serine, threonine and tyrosine residues, all targets for kinase-induced phosphorylation. Conversely, the carboxy terminus of the full-length hEP$_3$27 receptor contains all of these amino acids and thus has the potential to be regulated by phosphorylation (FIG. 1). It is important to understand the contribution of each of these variant receptors to the overall effect of the ligand since this overall effect is a sum of the effects exerted by the different receptors.

A full length functional eukaryotic expression plasmid was constructed as described in the following example.

EXAMPLE 5

Construction of a Functional EP$_3$ Expression Plasmid

To construct a full length plasmid encoding the human EP$_3$ receptor, a sense PCR primer (5'GATCCACCGCGGTGGAATATTGCCCCCTCCCGCT GCGGCTCT-3'; SEQ ID NO: 14) containing adjacent BstXI and SspI restriction sites was designed to have homology to a nucleotide sequence upstream of the hEP$_3$ $_{receptor}$ translation start site. This primer had sequences identical to the cDNA and genomic clones as well as an additional 5' sequence. This primer was used with a corresponding antisense primer (5'-GTCCAGTGGCCCGGGACGTGGTG-3'; SEQ ID NO:

15) in a PCR reaction with the 2.4 kb genomic clone as a template. A 700 base pair product was obtained, purified with Geneclean (Bio 101, Inc.) and digested with BstXI. The 500 base pair fragment was isolated from a low-melting-point agarose gel and was used in a solid phase ligation (Sambrook et al., 1989, Molecular Cloning: a Laboratory Manual, Cold Spring Harbor Laboratory) with the 4.2 kb fragment isolated from the digestion of pBluescript cDNA clone (hEP$_3$27) with BatXI. *E. coli* were transformed and a clone was obtained (KS/hEP$_3$ FulCod27) The full-length clone KS/hEP$_3$27 Ful/Cod obtained by this procedure had 1170 bases of the complete open reading frame, 56 bases of 5'-untranslated sequence and 504 bases of 3'-untranslated sequence (SEQ ID NO: 13). The putative transmembrane (TM) regions were encoded by the following nucleotide sequences of SEQ ID NO: 16; TM1, 211–277; TM2, 319–398; TM3, 451–511; TM4, 571–646, TMS, 739–814; TM6, 895–964; TM7, 1039–1102. A full-length hEP$_3$19 clone was made by ligation of the large fragment remaining from the digestion of KS/hEP$_3$27 Ful/Cod with BglII and HindIII with the small fragment remaining from the digestion of hEP$_3$19 with the same enzymes. A full-length hEP$_3$11 clone was made in a similar manner by digesting the hEP$_3$11 clone with BamHI and ligating the resulting small fragment to the large fragment remaining from the digestion of KS/hEP$_3$27 Ful/Cod with BamHI which had been previously modified by digestion with SspI and cloning the sequence back into pBluescript which had been cleaved with EcoRV.

The full length clone, KS/hEP$_3$27 FulCod (SEQ ID NO: 16), was digested with SspI, analyzed on a 1.4% agarose gel and the 1.4 kb fragment was then purified. The eukaryotic expression vector pBC12BI (Cullen, (1987) Methods Enzymol., 152: 684–704) was digested with BamHI and HindIII, treated with the Klenow fragment of DNA polymerase I to produce blunt ends and analyzed on a 1.4% low-melting point agarose gel. The 3.9 kb fragment was isolated and used in a solid phase ligation with the 1.4 kb SspI fragment from KS/hEP$_3$ FulCod/27. *E. coli* were transformed and a clone was obtained (pBC/hEP$_3$). The full-length hEP$_3$19 was inserted into the pBC12BI vector in the same manner except that it was digested with HinfI and made blunt-ended with the Klenow fragment of DNA polymerase I prior to SspI digestion. The full-length hEP$_3$11 was digested with HindIII and SspI and ligated into the pBC12BI vector that had been digested with BamHI, blunt-ended with the Klenow fragment of DNA polymerase I and then digested with HindIII.

So as to perform the necessary binding assays for demonstrating the ligand specificity of the protein derived from the isolated clone, the hEP$_3$ receptor was expressed in transfected COS-7 cells as described in the following example.

EXAMPLE 6

Expression of the Human EP$_3$27 Receptor in COS-7 Cells

Monolayers of COS-7 cells (70–80% confluent) were rinsed with Phosphate Buffered Saline (PBS, Ca/Mg-free) in 150×25 mm culture dishes. Ten ml transfection mix, consisting of 5 µg/ml plasmid DNA, 0.5 mg/ml DEAE-dextran in PBS, was added to each dish and cells were incubated for 30 min at 37° C. Nine mls of the solution was removed from each dish followed by the addition of 10 ml of 100 mM chloroquine in Dulbecco's Modified Eagle Medium (DMEM)/5% fetal bovine serum (FBS). The cells were incubated for 2.5 hr at 37° C., the solution aspirated and 10 ml of 10% dimethyl sulfoxide (DMSO) in DMEM/5% FBS was added. The cells were incubated for 2.5 minutes at 37° C., the solution was aspirated and 30 ml of DMEM/5% PBS was added. The cells were incubated at 37° C. with media changes at 24 and 48 hours. The media was aspirated after 72 hours and the cells were scraped into cold TME buffer (50 mM Tris-HCl, pH 7.4, 10 mM MgCl$_2$, 1 mM EDTA) The dishes were rinsed with cold TME buffer and the cells combined and placed on ice.

To demonstrate the binding of hEP$_3$ receptor ligands to isolated membranes of COS-7 cells expressing the hEP$^3$27 receptor, membranes were isolated and the binding of radiolabeled ligands was assessed in the presence of increasing concentrations of unlabeled prostaglandin receptor agonists as described in the following example:

EXAMPLE 7

COS-7 Membrane Preparation and Radioligand Binding Assay

Transfected COS-7 cells were homogenized for 30 seconds at approximately 80% power with a Brinkman PT 10/35 Polytron. The homogenate was centrifuged at 19,000 rpm for 20 minutes at 4° C. using a Sorvall SS-34 rotor. The membrane pellet was resuspended in cold TME buffer (1 ml per original dish), frozen in liquid nitrogen and stored at –80° C.

Membrane pellets were resuspended in ice-cold 50 mM Tris-HCl buffer at pH 7.4 by using a sonicator at the 50 watt setting. Membrane suspensions (100 µl) were then added to each assay tube to start the binding reaction. Final concentrations were as follows: [$^3$H-PGE$_2$, 5 nM; 60–70 µg protein/tube in a total volume of 200 µl. Samples were incubated for 30 minutes at room temperature. Contents were aspirated onto a presoaked ice-cold Whatman GF/B filter using a Brandel Cell Harvester and washed three times with ice-cold assay buffer. The filters were dried, placed in scintillation fluid and counted.

Figure 2:
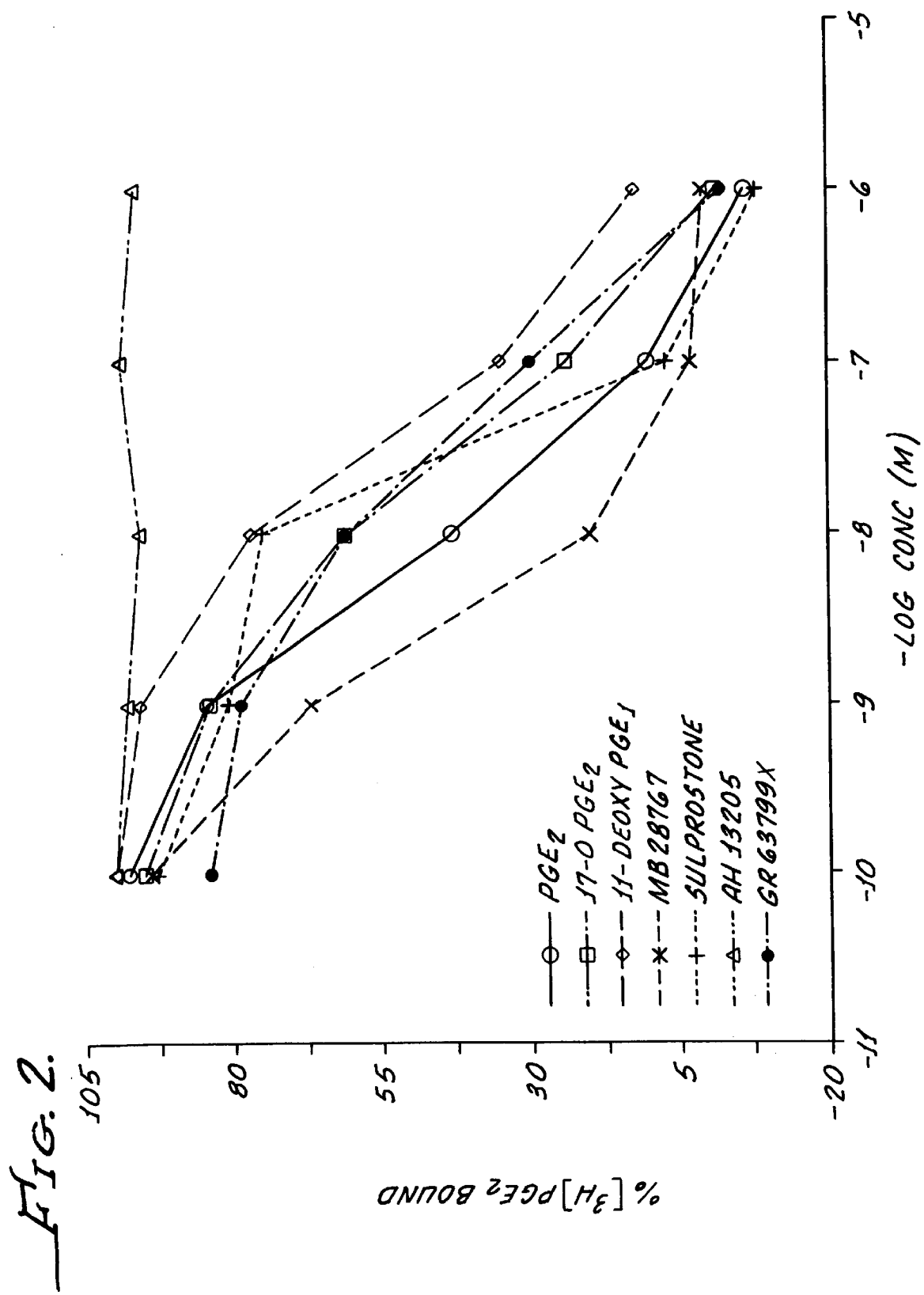
FIG. 2 illustrates a second competition curve of [$^3$H]PGE$_2$ binding to membranes from COS-7 cells transfected with the full-length $hEP_3$27 $EP_3$ receptor in order to more precisely define the subtype of the cloned receptor. The y-axis indicates the percentage of [$^3$H]PGE$_2$ specifically bound and the x-axis indicates the concentration of competitor added (-log M).

As shown in FIG. 2, as expected, the strongest competitor of [$^3$H]-PGE$_2$ binding was PGE$_2$ itself. PGE$_1$ was also an effective competitor and is known to bind to the hEP$_3$ receptor. However, PGF$_{2\alpha}$ and PGD$_2$, prostaglandins specific for the FP and DP receptors, respectively, competed weakly but only at higher concentrations. The Thromboxane A$_2$ analogue U46619 was totally ineffective in competing for [$^3$H]-PGE$_2$ binding (FIG. 2).

Figure 3:
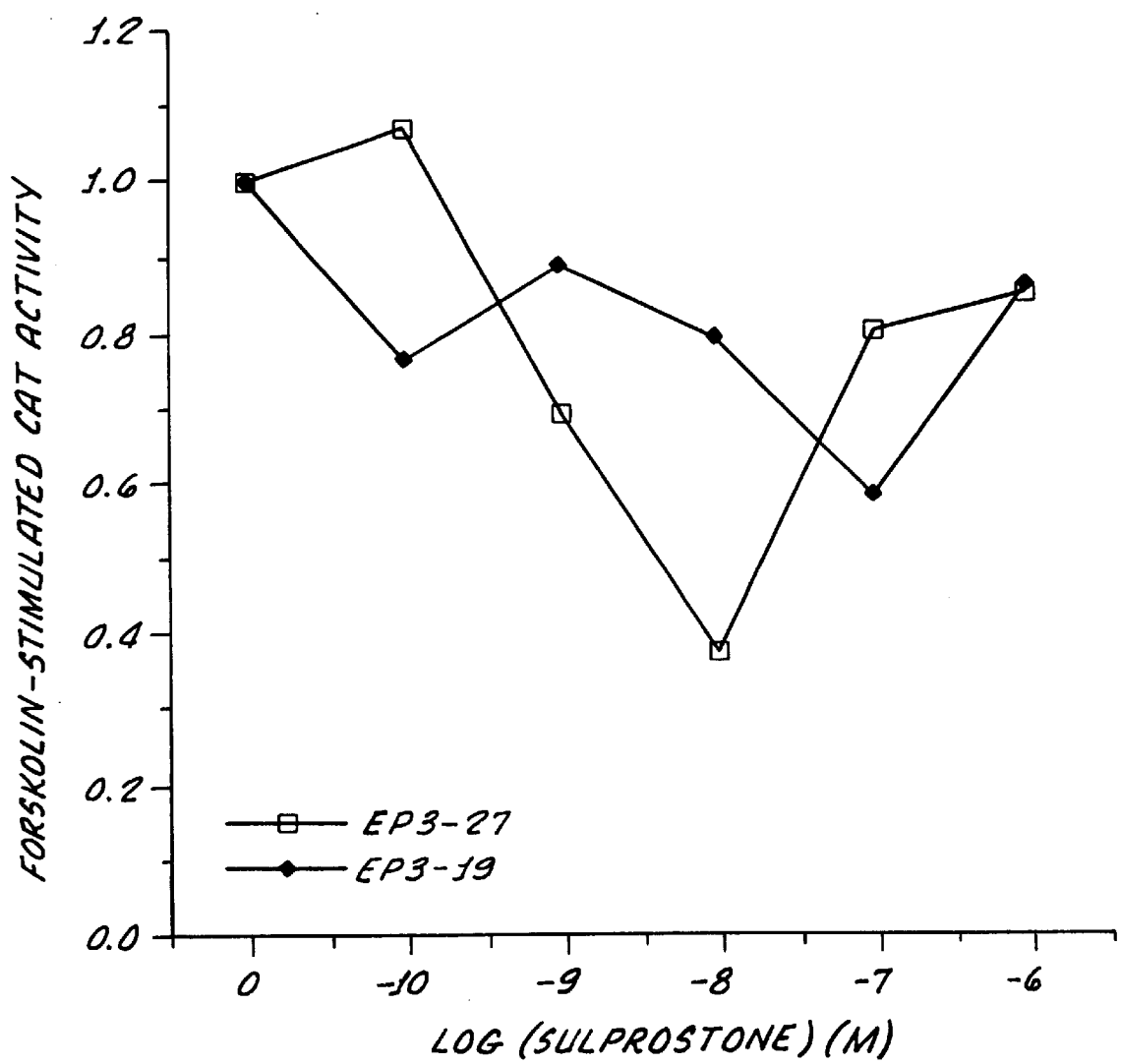
FIG. 3 is a graph showing the effects of sulprostone on forskolin-stimulated chloramphenicol acetyltransferase (CAT) reporter gene activity after transient transfector of JEG-3 cells with DNA encoding the reporter gene and the full-length $hEP_3$27 or the splice variant $hEP_3$19. The sulprostone concentration (-log M) is indicated on the x-axis and the CAT activity is indicated on the y-axis.

FIG. 3 shows additional agonist competition data which further defined the receptor subtype. MB28767, an EP$_3$ receptor-selective agonist, was the most potent competitor of [$^3$H]-PGE$_2$ binding. In fact, this compound was even more potent that PGE$_2$ itself. GR63799X and sulprostone, two EP$_3$ receptor agonists, also competed significantly for [$^3$H]-PGE$_2$ binding. The PGE$_1$ and PGE$_2$ analogs, 11-deoxy PGE$_1$ and 17-phenyl PGE$_2$, respectively, also competed but not as well as the parent compounds. AH13205, an EP$_2$-selective agonist, did not compete.

An important difference between the mouse EP$_3$ receptor and the human EP$_3$ receptor is the binding affinity for various receptor agonists. Sugimoto et al. (*J. Biol. Chem.* (1990) 267: 6463–6466) determined that the binding affinity of PGE$_1$, PGE$_2$, MB28767 and GR63799X for the murine receptor were all very similar. However, the binding affinity of these compounds for the expressed human receptor was quite different with MB28767>PGE$_2$>PGE$_1$=GR63799X. This indicates that the two receptors might differ in their response to the same agonists and further that there may be important functional differences between the two receptors.

The native $EP_3$ receptor is coupled through a G protein to the inhibition of adenylate cyclase, an enzyme which converts ATP to cyclic AMP (cAMP). To produce a sensitive functional assay for prostaglandin receptor binding, the $hEP_327$ cDNA was cotransfected with a cAMP-dependent CAT reporter plasmid into human JEG-3 choriocarcinoma cells. The effects of $EP_3$ receptor agonists on forskolin-induced cAMP accumulation are described in the following example.

EXAMPLE 8

Drug Treatment and CAT Assay

Human JEG-3 cells (American Type Culture Collection, Rockville, Md.) were cultured in DMEM containing 10% FCS, 100 units/ml penicillin, 100 µg/ml streptomycin. Cells were plated in 10 cm dishes 1–2 days before transfection. Cells were then transfected with 10 µg of a CAT reporter plasmid TESBgIICRE(+)ΔNHSE (provided by P. Mellon, Salk Institute, La Jolla, Calif.) containing an 18 base pair cyclic AMP responsive element from the promoter of the α-subunit gene for the human glycoprotein hormones linked to the herpes simplex virus thymidine kinase promoter in turn linked to CAT (Delegeane et al., (1987) *Mol. Cell. Biol.*, 7: 3994–4002), and 10 µg $hEP_3$ receptor plasmid, using the calcium phosphate precipitation technique (Graham and van der Eb, (1973) *Virology*, 52: 456–467). After transfection, cells were maintained in DMEM/5% FCS for 36–40 hours. They were then rinsed twice with DMEM. Forskolin (1 µM), a drug known to stimulate adenylate cyclase activity, and sulprostone, an $EP_3$ receptor agonist, were then added in 5 ml DMEM. Cells were incubated for 4 hours at 37° C. and harvested.

For the CAT assay, after drug incubations, cells were rinsed with cold PBS and scraped into 1 ml 40 mM Tris-HCl, pH 7.5, 150 mM NaCl, 1 mM EDTA. Cells were centrifuged and lysed by 3 cycles of freeze-thaw in 200 µl 250 mM Tris-HCl, pH 7.5. ($^3$H]-CAT assays were performed using 50 µl cytosol, 200 nCi [$^3$H]-chloramphenicol and 300 µM butyryl CoA (Seed and Sheen, (1988) *Gene*, 67: 271–277). Samples were incubated for 1 hour at 37° C. and reactions were stopped by addition of 200 µl mixed xylenes. Butyrylated chloramphenicol was extracted into mixed xylenes which were back extracted twice with 200 µl 10 mM Tris-HCl, pH 8.0, 1 mM EDTA. Radiolabeled product was measured by liquid scintillation counting using a Packard Tri-Carb 460C at 50–52% efficiency. Increased CAT activity, indicated by transfer of butyryl groups from butyryl CoA to [$^3$H]-chloramphenicol, was a measure of increased cAMP accumulation.

$hEP_327$ and CRE-CAT cotransfected JEG-3 cells exhibited a biphasic response to increasing concentrations of sulprostone, with inhibition of CAT activity occurring at low concentrations and a reversal occurring at higher concentrations (FIG. 4). This biphasic response was not reported for the mouse $EP_3$ receptor and further demonstrates the functional differences between the murine and human $EP_3$ receptors.

To determine whether any functional differences existed between the full-length $hEP_327$ clone and the splice variants, COS-7 cells were cotransfected with the $hEP_319$ clone. The CAT assay was performed and the dose-response profile was compared to that of $hEP_327$. As indicated in FIG. 4, the dose-response curves of the two clones are clearly different. The $hEP_327$ clone is more sensitive to sulprostone than the $hEP_319$ clone. This indicates that the clones are functionally as well as sequentially different and exhibit different pharmacologies that cannot be predicted from previous results.

EXAMPLE 9

Tissue Distribution of $EP_3$ Receptor Gene

A multiple human tissue Northern blot (Clontech) consisting of RNA isolated from heart, brain, placenta, lung, liver, kidney and pancreas was prehybridized in 4.4×SSPE, 44% deionized formamide, 8.8×Denhardt's solution, 1.75% SDS and 88 µg/ml denatured herring sperm DNA to reduce background hybridization at 42° C. with constant rotation. The prehybridization solution was removed and the filter was incubated in fresh solution containing 1.5×10$^6$ cpm/ml nick-translated $hEP_3$/27/FulCod DNA (Gibco BRL, Gaithersburg, Md.) at 42° C. overnight with constant rotation. The blot was washed six times in 2×SSC, 0.5% SDS at room temperature for 5 minutes each with constant agitation. The blot was then washed in 0.1×SSC, 0.1% SDS at 50° C. for 40 minutes with one change of solution, dried and exposed to x-ray film. The lane containing the kidney RNA was strongly positive, while the lanes containing the heart and pancreas RNA were much weaker in intensity.

EXAMPLE 10

Production of Polyclonal Antibodies Against Human $EP_3$

PCR primers are used to amplify an 80 nucleotide region corresponding to the hydrophilic amino acid segments connecting the fifth and sixth membrane spanning domains of the human $EP_3$ receptor. The resulting PCR product is purified by agarose gel electrophoresis, cloned into an expression plasmid such as PGEX (Pharmacia, Piscataway, N.J.) and used to transform *E. coli* by standard procedures. The positive clones are identified and induced to express the fusion protein, which is purified by well known methods.

The purified fusion protein is injected into the breast muscle of chickens (50–100 µg/injection) with booster injections given at two week intervals. The IgY antibodies are purified from the egg yolks by well known methods and their specificity determined by immunoblotting of tissue extracts.

In addition, monoclonal antibodies to the $hEP_3$ receptor can be prepared as discussed below.

EXAMPLE 11

Production of Monoclonal Antibodies Against $EP_3$

The $hEP_3$ receptor-transfected COS-7 cell lysate, isolated as described in Example 6, is centrifuged to isolate membranes. The isolated membranes are injected in Freund's complete adjuvant into mice. After 9 booster injections over a three week period, the spleens are removed and resuspended in PBS. The resuspended spleen cells are mixed (approximately 4:1) with SP2/0 myeloma cells. Polyethylene glycol is added to fuse the myeloma and spleen cells, and the hybridomas are selected in HAT medium. The fused cells are aliquoted to allow growth of only one cell in each well of a 96 well microtiter plate. Each cell is expanded, the media removed and secreted proteins are labeled with $^{125}$I. The labeled media from each well is used to probe a Western blot of transfected and untransfected COS-7 cell membranes.

The desired hybridoma produces a monoclonal antibody that strongly binds a protein band in a transfected COS-7 cell membrane lane on a Western blot, but does not bind to any other protein in that lane or in an untransfected COS-7 cell membrane lane (control). This method can be used to detect those cells expressing the human $EP_3$ receptor.

EXAMPLE 12

Production of Stably-transefected Cells

To produce CHO cells stably transfected with the $hEP_3$ gene, CHO cells are cotransfected with 10–30 μg $hEP_3$ (SEQ ID NO; 13) and 1–5 μg pSV2Neo carrying the neomycin resistance gene by calcium phosphate precipitation (Graham and Van der Eb, (1973) *Virology*, 52; 456–467). The cells are then subjected to selection with 600 μg/ml genetecin (G418; Gibco). The resistant colonies are selected, expanded and screened for receptor expression using [$^3$H]$PGE_2$ binding as described in Example 7.

While particular embodiments of the invention have been described in detail, it will be apparent to those skilled in the art that these embodiments are exemplary, rather than limiting, and the true scope of the invention is that defined in the following claims.

What is claimed is:

1. A method of identifying modulators of a human prostaglandin $EP_3$ receptor comprising the steps:
   i) contacting a test compound with an isolated or recombinant human $EP_3$ receptor; and
   ii) directly or indirectly measuring the effect, if any, of said compound on an activity of said $EP_3$ receptor as an indication of whether said compound is a modulator of said $EP_3$ receptor protein.

2. The method of claim 1 wherein said measured effect is the ability of said compound to bind to said $EP_3$ receptor.

3. The method of claim 2, wherein compound inhibits $EP_3$ receptor binding by a ligand selected from the group consisting of $PGE_2$, $PGE_1$, $PGF_{2\alpha}$, $PGD_2$, 11-deoxy $PGE_1$, sulprostone, and 17-phenyl $PGE_2$.

4. The method of claim 1 wherein said measured effect is the stimulation of ligand-mediated $EP_3$ receptor activity.

5. The method of claim 4 wherein said stimulation is measured as a decrease in adenylate cyclase activity.

6. The method of claim 1 wherein said measured effect is the inhibition of ligand-mediated $EP_3$ receptor activity.

7. The method of claim 6 wherein said inhibition is measured as an increase in adenylate cyclase activity.

* * * * *

UNITED STATES PATENT AND TRADEMARK OFFICE
CERTIFICATE OF CORRECTION

PATENT NO.     : 6,670,134 B1                                    Page 1 of 1
DATED          : December 30, 2003
INVENTOR(S)    : Gil et al.

It is certified that error appears in the above-identified patent and that said Letters Patent is hereby corrected as shown below:

Column 1,
Line 37, delete "(EP3)" and insert in place thereof -- (EP$_3$) --

Column 5,
Line 28, delete "The" and insert in place thereof -- These --
Line 40, delete "Tag" and insert in place thereof -- Taq --

Signed and Sealed this

First Day of June, 2004

JON W. DUDAS
*Acting Director of the United States Patent and Trademark Office*